(12) United States Patent
Ahmed

(10) Patent No.: US 12,208,266 B2
(45) Date of Patent: *Jan. 28, 2025

(54) MULTI-SITE NEUROMODULATION FOR TREATMENT OF ALS AND RELATED DISORDERS

(71) Applicant: Research Foundation of the City University of New York, New York, NY (US)

(72) Inventor: Zaghloul Ahmed, Staten Island, NY (US)

(73) Assignee: Research Foundation of the City University of New York, New York, NY (US)

(*) Notice: Subject to any disclaimer, the term of this patent is extended or adjusted under 35 U.S.C. 154(b) by 465 days.

This patent is subject to a terminal disclaimer.

(21) Appl. No.: 17/331,142

(22) Filed: May 26, 2021

(65) Prior Publication Data

US 2021/0393958 A1 Dec. 23, 2021

Related U.S. Application Data

(60) Provisional application No. 63/029,816, filed on May 26, 2020, provisional application No. 63/187,116, filed on May 11, 2021, provisional application No. 63/187,745, filed on May 12, 2021.

(51) Int. Cl.

| A61N 1/36 | (2006.01) |
|---|---|
| A61N 1/05 | (2006.01) |
| A61N 1/20 | (2006.01) |
| A61N 1/378 | (2006.01) |

(52) U.S. Cl.
CPC ....... *A61N 1/36067* (2013.01); *A61N 1/0551* (2013.01); *A61N 1/205* (2013.01); *A61N 1/36062* (2017.08); *A61N 1/3787* (2013.01)

(58) Field of Classification Search
CPC .............. A61N 1/0551; A61N 1/36062; A61N 1/36067
See application file for complete search history.

(56) References Cited

U.S. PATENT DOCUMENTS

| 4,919,140 | A | 4/1990 | Borgens et al. |
|---|---|---|---|
| 8,380,304 | B2 | 2/2013 | Lozano |
| 9,283,391 | B2 | 3/2016 | Ahmed |
| 11,331,424 | B2 | 5/2022 | Imran et al. |
| 2005/0119712 | A1 | 6/2005 | Shafer |

(Continued)

FOREIGN PATENT DOCUMENTS

| EP | 3581239 | 5/2021 |
|---|---|---|
| WO | WO2006053186 | 5/2006 |

(Continued)

OTHER PUBLICATIONS

ISA/US; International Search Report/Written Opinion for PCT/US2016/018167 mailed May 2, 2016.

(Continued)

*Primary Examiner* — Alyssa M Alter
(74) *Attorney, Agent, or Firm* — Peter J. Mikesell; Schmeiser, Olsen & Watts, LLP

(57) ABSTRACT

Methods and systems for treating ALS and related motor neuron diseases using multi-site neuromodulation are disclosed.

33 Claims, 16 Drawing Sheets
(5 of 16 Drawing Sheet(s) Filed in Color)

(56) References Cited

U.S. PATENT DOCUMENTS

| | | |
|---|---|---|
| 2005/0267103 A1 | 12/2005 | Hochman |
| 2010/0274305 A1 | 10/2010 | Gliner et al. |
| 2013/0035745 A1 | 2/2013 | Ahmed et al. |
| 2013/0053922 A1 | 2/2013 | Ahmed et al. |
| 2013/0090542 A1 | 4/2013 | Kipke et al. |
| 2014/0017214 A1 | 1/2014 | Cost |
| 2014/0148872 A1 | 5/2014 | Goldwasser et al. |
| 2014/0249601 A1 | 9/2014 | Bachinski et al. |
| 2014/0302007 A1 | 10/2014 | Blanda et al. |
| 2015/0239832 A1 | 8/2015 | Hochman et al. |
| 2017/0312505 A1 | 11/2017 | Ahmed |
| 2018/0071525 A1 | 3/2018 | Ahmed |
| 2019/0201684 A1* | 7/2019 | Williams ........... A61N 1/36025 |
| 2020/0101291 A1 | 4/2020 | Yakovlev et al. |
| 2021/0128920 A1 | 5/2021 | Grill et al. |

FOREIGN PATENT DOCUMENTS

| | | |
|---|---|---|
| WO | WO2006110187 | 10/2006 |
| WO | WO2012018635 | 2/2012 |
| WO | WO2014039454 | 3/2014 |
| WO | WO2015095880 | 6/2015 |
| WO | WO2016133960 | 8/2016 |
| WO | WO2016209997 | 12/2016 |
| WO | WO2019183536 | 9/2019 |
| WO | WO-2019183536 A1 * | 9/2019 ........... A61K 31/196 |

OTHER PUBLICATIONS

EPO; European Supplementary Partial Search Report mailed Jan. 17, 2022 for related European Application 19772271.3.

Ahmed, Z.; Trans-Spinal Direct Current Stimulation Alters Muscle Tone in Mice with and without Spinal Cord Injury with Spasticity; The Journal of Neuroscience; Jan. 29, 2014; pp. 1701-1709; 34(5).

Gifondorwa, D. et al.; Exogenous Delivery of Heat Shock Protein 70 Increases Lifespan in a Mouse Model of Amyotrophic Lateral Sclerosis; The Journal of Neuroscience; Nov. 28, 2007; pp. 13173-13180; 27(48).

Robinson, M. et al.; Extracellular Heat Shock Protein 70: A Critical Component for Motoneuron Survival; The Journal of Neuroscience; Oct. 19, 2005; pp. 9735-9745; 25(42).

Keuters, M. et al.; Transcranial direct current stimulation promotes the mobility of engrafted NSCs in the rat brain; NBR in Biomedicine; Dec. 17, 2014; pp. 231-239; vol. 28.

McKenzie, I. et al.; Motor skill learning requires active central myelination; Research; Oct. 17, 2014; pp. 318-322; vol. 346, Issue 6207.

Brashear; A.; Botulinum toxin type A in the treatment of patients with cervical dystonia; Biologics: Targets & Therapy; 2009; vol. 3.

Hsieh, P. et al.; Effect of acetazolamide for long-lasting paroxysmal dystonia in a patient with multiple sclerosis: a case report and review of literature; Neuropsychiatric Disease and Treatment; 2013; pp. 445-448; vol. 9.

ISA/US; International Search Report/Written Opinion for PCT/US2019/023675 mailed Jul. 7, 2019.

ISA/US; International Search Report/Written Opinion for related International Application PCT/US2022/030655 mailed Sep. 2, 2022.

EPO; Extended European Search Report mailed Nov. 4, 2022 in related European Application 19772271.3.

* cited by examiner

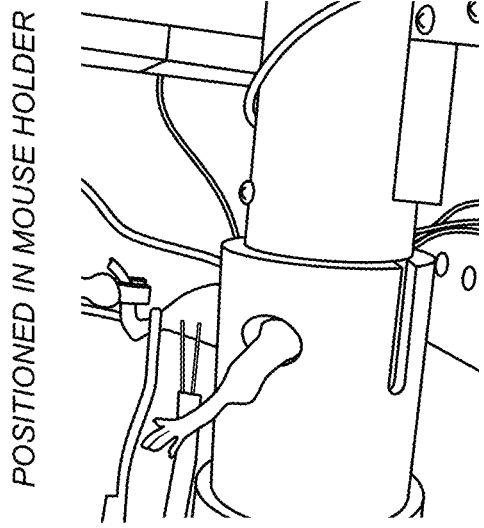
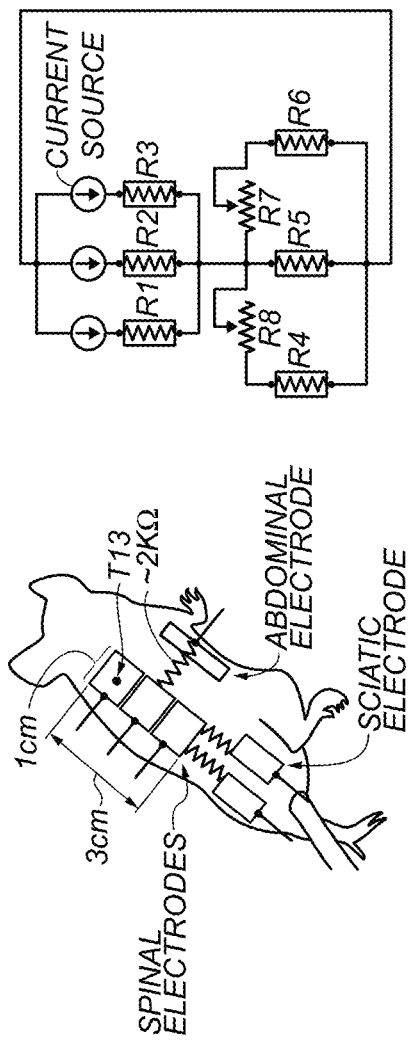
FIG. 1A  MULTI-SITE DCS SETUP
FIG. 1B
FIG. 1C  POSITIONED IN MOUSE HOLDER
TRANSGENIC ALS MICE (SOD1$^{G93A}$) DEVELOP MUSCLE TREMOR, PARALYSIS AND PREMATURE DEATH ARE GOLD STANDARD PRECLINICAL MODEL OF ALS
TRANSGENIC ALS MICE DEVELOP TREMOR AND PARALYSIS

EMG SHOWS SUPPRESSION OF ACTIVITY WITH STIMULATION

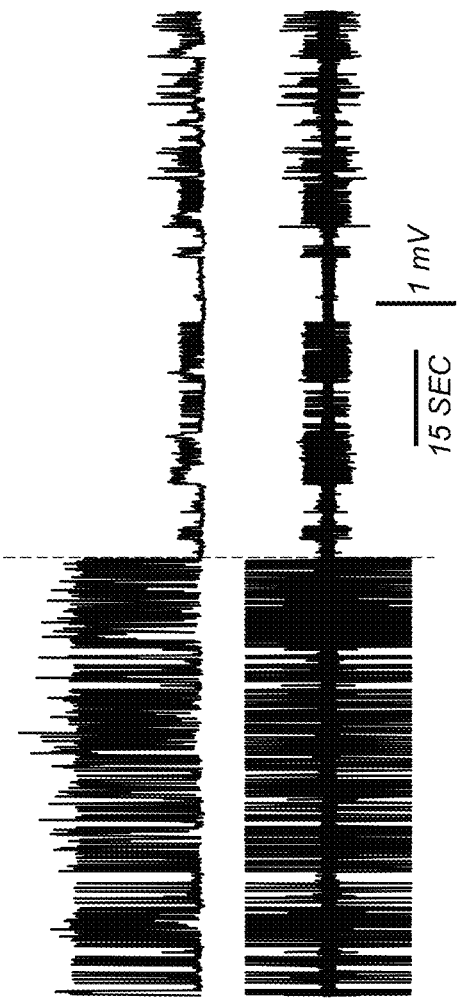
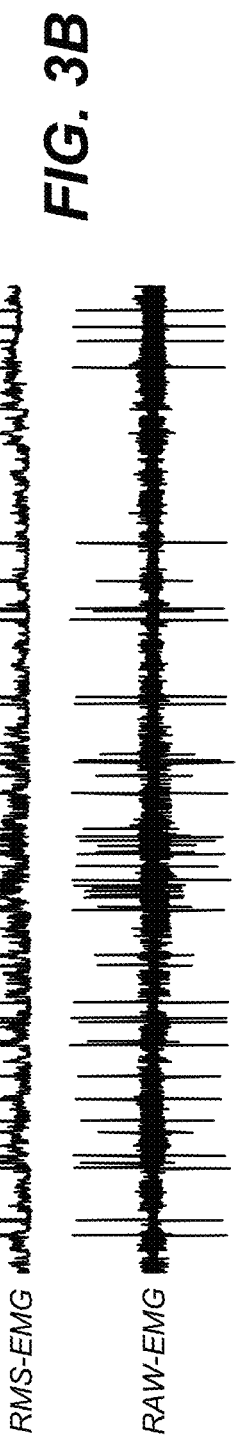

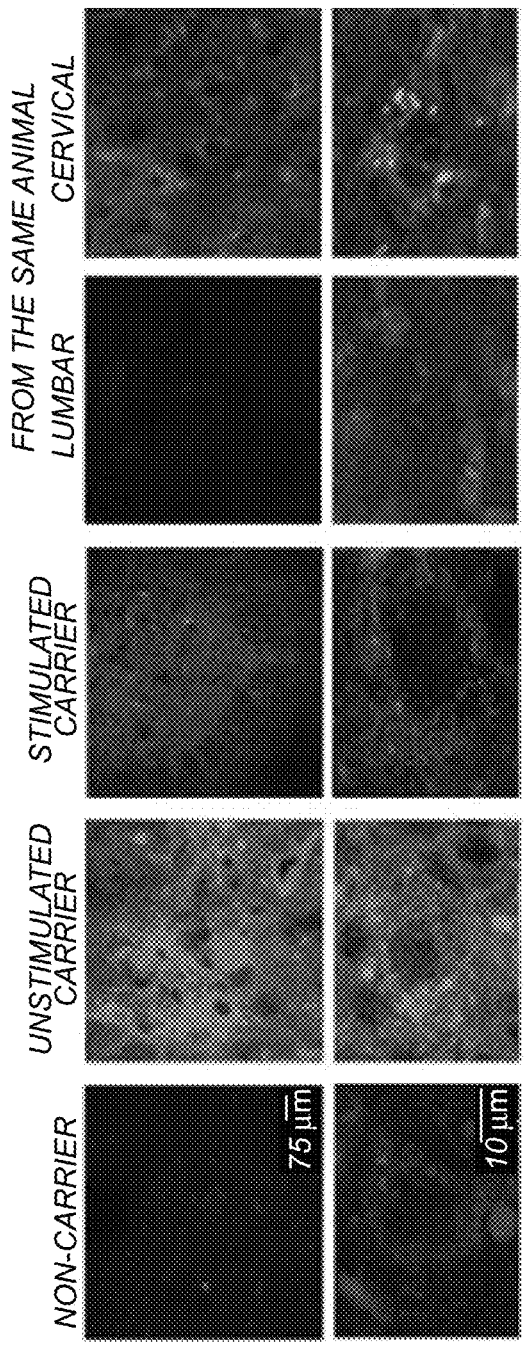
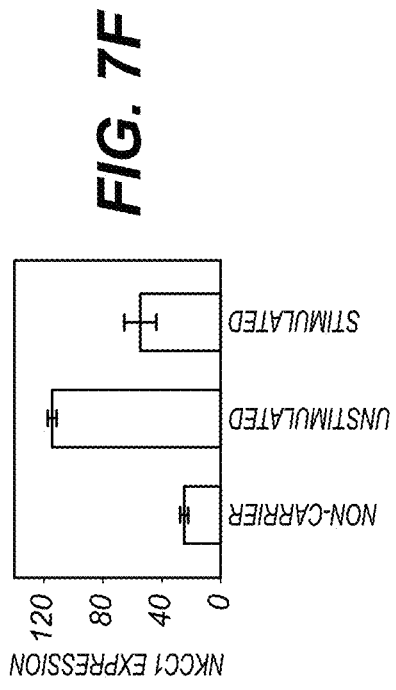
FIG. 7A FIG. 7B FIG. 7C FIG. 7D FIG. 7E
FIG. 7F

*ELEVATED SOD1 EXPRESSION REDUCED BY STIMULATION*
FIG. 8A *CONTROL CARRIER*  FIG. 8B *STIMULATED CARRIER*
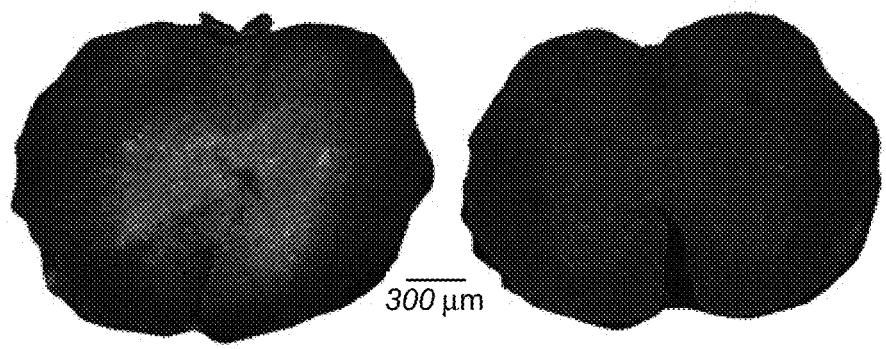
300 μm
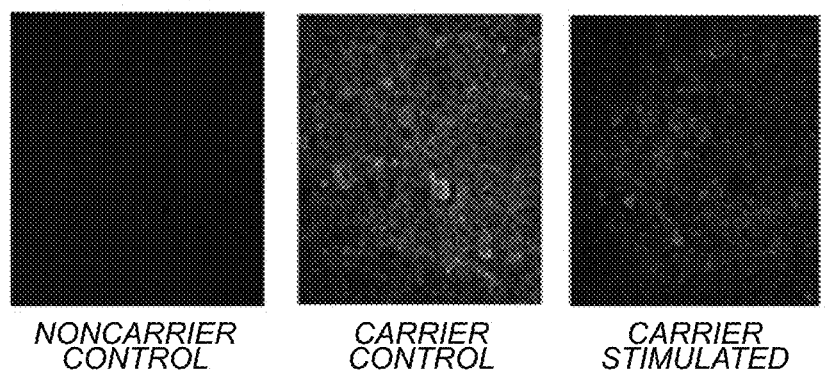
*NONCARRIER CONTROL*  *CARRIER CONTROL*  *CARRIER STIMULATED*
FIG. 8C  FIG. 8D  FIG. 8E
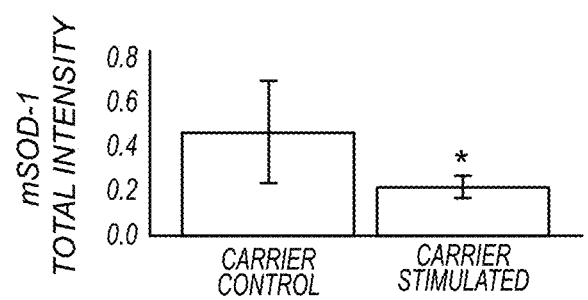
FIG. 8F

STIMULATION REDUCES PHOSPHORYLATED TAU

Ph-tau LABELLED AT P231

PHOSPHORYLATED TAU IS INVOLVED IN ALS[1]
MORE Ph-tau IS FOUND IN ALS MICE THAN IN CONTROLS
STIMULATION REDUCES Ph-tau LEVELS IN ALS MICE 1: STEVENS ET AL., "INCREASED TAU PHOSPHORYLATION IN MOTOR NEURONS FROM CLINICALLY PURE SPORADIC AMYOTROPHIC LATERAL SCLEROSIS PATIENTS", J. NEUROPATHOL. EXP. NEUROL. 2019

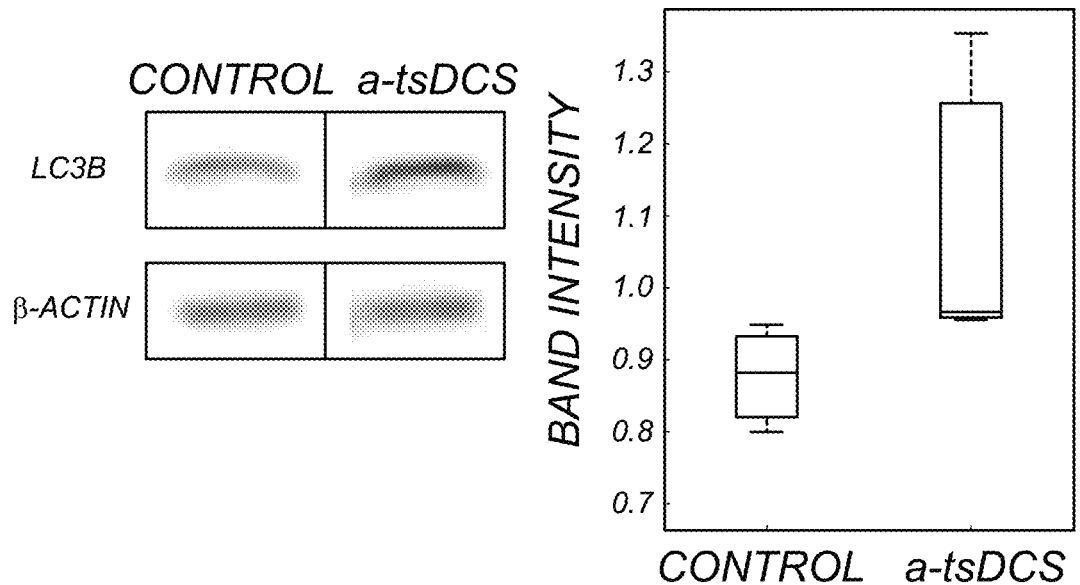

LC3B EXPRESSION IS UPREGULATED BY ANODAL MULTI-SITE DCS. ANODAL MULTI-SITE DCS SIGNIFICANTLY INCREASES LC3B EXPRESSION IN SPINAL CORDS OF SOD1-G93A MICE. LC3B EXPRESSION WAS QUANTIFIED BY EVALUATING THE INTENSITY OF WESTERN BLOT BANDS OF SPINAL CORD EXTRACTS USING IMAGJ. ANIMALS WERE STIMULATED ONCE FOR 40 MINUTES. BOX GRAPH REPRESENTS STIMULATED ANIMALS (n=5) AND CONTROL ANIMALS (n=4).

FIG. 11

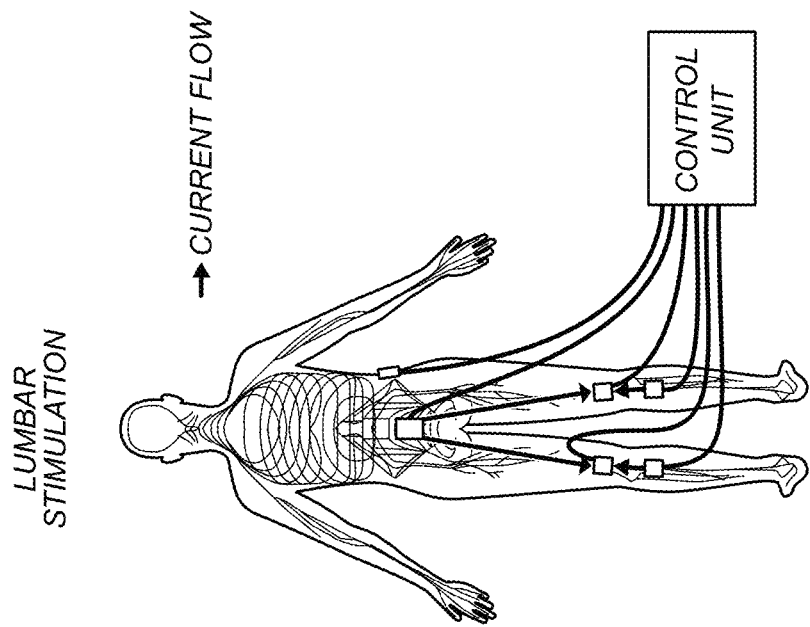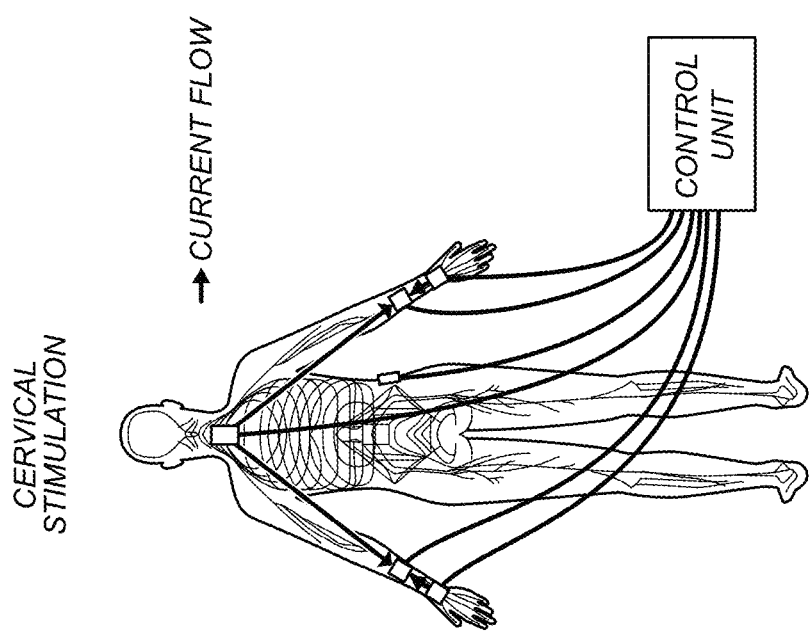
FIG. 15

MULTI-SITE NEUROMODULATION FOR TREATMENT OF ALS AND RELATED DISORDERS

CROSS-REFERENCE TO RELATED APPLICATIONS

This application claims priority to U.S. provisional patent applications 63/029,816 (filed May 26, 2020); 63/187,116 (filed May 11, 2021) and 63/187,745 (filed May 12, 2021), the content of which are incorporated herein by reference for all purposes.

FIELD

The present invention relates to methods and systems based on multi-site neuromodulation for treating amyotrophic lateral sclerosis (ALS) and related neurological disorders.

BACKGROUND

Amyotrophic lateral sclerosis (ALS, Lou Gehrig's disease, Charcot's disease) is a rapidly fatal progressive neurodegenerative disease that affects multiple neuronal networks. The disease is the result of a systematic dismantling of the motor neuron system, with clinical manifestations dependent on site of onset; the relative affinity of the dismantling process for prefrontal, upper and lower motor neurons; and the rate of the disease's spread within the network (Ravits et al., "ALS motor phenotype heterogeneity, focality, and spread: deconstructing motor neuron degeneration", *Neurology*, 2009). ALS results in muscle weakness, spasticity, paralysis and eventual death, typically within 2-5 years of diagnosis. Spasticity, a painful condition associated with spinal motor neuron hyperexcitability, is found in approximately 80% of ALS patients (Milinis et al., "Development and validation of Spasticity Index-Amyotrophic Lateral Sclerosis", *Acta. Neurol. Scand.*, 2018), and is primarily treated with injected botulinum neurotoxin or oral baclofen. Mechanism-specific treatments directed at the processes that cause ALS to evolve after it has expressed itself sufficiently to be diagnosed may, at best, have an ameliorative effect (Miller et al., "Practice parameter: the care of the patient with amyotrophic lateral sclerosis (an evidence-based review): report of the Quality Standards Subcommittee of the American Academy of Neurology: ALS Practice Parameters Task Force", *Neurology*, 1999). Treatments that halt the spread of the disease may be more effective than those that try to salvage affected motor neurons, though such treatments have yet to be realized. Currently, the mainstay of ALS therapy consists of adaptive treatments directed at the clinical manifestations of the disease (Bedlack and Mitsumoto, "Amyotrophic lateral sclerosis: a patient care guide for clinicians", *Demos Medical*, 2012). There are only 3 FDA-approved drugs for the treatment of ALS, all with very limited effectiveness. There is tremendous unmet medical need for non-invasive treatment of ALS.

While the majority of cases (90-95%) of ALS are sporadic and occur in patients without known familial history of ALS, the remaining 5-10% of cases are familial. There are at least 31 different gene mutations that have been associated with familial ALS (Mathis et al., "Genetics of amyotrophic lateral sclerosis: a review", *J. Neurol. Sci.*, 2019), and the most common types of familiar ALS are shown in Table 1:

TABLE 1

Most common subtypes of familial ALS by gene mutation

| Mutation | % of familial ALS | Predominant dysfunction (7) |
| --- | --- | --- |
| C9orf72 | 30% | Both UMN and LMN |
| SOD1 | 20% | Both UMN and LMN, but LMN becomes dominant with disease progression |
| TARDBP | 5% | Both UMN and LMN |
| FUS | 5% | Both UMN and LMN, but LMN becomes dominant with disease progression |

Clinical presentation in ALS includes fasciculations, muscle cramps, hyper-reflexia and spasticity, which typically progresses to shortness of breath, ventilatory dysfunction and eventual respiratory failure. ALS patients can exhibit both UMN and LMN symptoms. UMN symptoms include spasticity, weakness and increased reflexes, while LMN symptoms include muscle atrophy, weakness, fasciculations and decreased reflexes. Patients with ALS often complain of painful muscle cramps, spasms and spasticity. Patients with primary lateral sclerosis (PLS), a phenotype associated with predominant UMN impairment, can have severe spasticity (Singer et al., "Primary lateral sclerosis", *Muscle Nerve*, 2007).

Recent research has established important links between ALS and motor neuron hyperexcitability (Bae et al., "The puzzling case of hyperexcitability in amyotrophic lateral sclerosis", *J. Clin. Neurol.*, 2013; ElBasiouny et al., "Persistent inward currents in spinal motoneurons: important for normal function but potentially harmful after spinal cord injury and in amyotrophic lateral sclerosis", *Clin. Neurophysiol.*, 2010; Kiernan et al., "Amyotrophic lateral sclerosis: origins traced to impaired balance between neural excitation and inhibition in the neonatal period", *Muscle and Nerve*, 2019; Mòdol et al., "Prevention of NKCC1 phosphorylation avoids downregulation of KCC2 in central sensory pathways and reduces neuropathic pain after peripheral nerve injury", *Pain*, 2014; Pieri et al., "Altered excitability of motor neurons in a transgenic mouse model of familial amyotrophic lateral sclerosis", *Neurosci. Lett.*, 2003; Wainger et al., "Intrinsic membrane hyperexcitability of amyotrophic lateral sclerosis patient-derived motor neurons", *Cell Rep.*, 2014). The premise is that hyperexcitable motor neurons depolarize easily, become fatigued, and eventually die, leading to weakness and paralysis in the muscles innervated by those motor neurons. Human neurophysiological studies using nerve conduction testing demonstrated axonal hyperexcitability of motor neurons in both sporadic and familial types of ALS (Bostock et al., "Axonal ion channel dysfunction in amyotrophic lateral sclerosis", *Brain*, 1995; Vucic and Kiernan, "Upregulation of persistent sodium conductances in familial ALS", *J. Neurol. Neurosurg. Psychiatry*, 2010), and hyperexcitability has been reported in other ALS subtypes (Blair et al., "FUS mutations in amyotrophic lateral sclerosis: clinical, pathological, neurophysiological and genetic analysis", *J. Neurol. Neurosurg. Psychiatry*, 2010; Williams et al., "Pathophysiological insights into ALS with C9ORF72 expansions", *J. Neurol. Neurosurg. Psychiatry*, 2013), suggesting that motor neuron hyperexcitability is consistently found across different ALS variants. Cortical hyperexcitability has also been shown in ALS, and is an early feature of ALS which may precede muscle weakness onset (Vucic and Kiernan, "Axonal excitability properties in amyotrophic lateral sclerosis", *Clin.*

*Neurophysiol.*, 2006; Vucic et al., "Cortical hyperexcitability may precede the onset of familial amyotrophic lateral sclerosis", *Brain*, 2008).

Our group reported in 2019 the first direct link between overexpression of a specific neuronal co-transporter and the emergence of spasticity (Mekhael et al., "Repeated anodal trans-spinal direct current stimulation results in long-term reduction of spasticity in mice with spinal cord injury", *J. Physiol.*, 2019), a condition also associated with motor neuron hyperexcitability. This Na—K—Cl cotransporter (NKCC1) is found on motor neurons and is involved in maintaining chloride gradient. We reported that in an animal model of spinal cord injury, NKCC1 becomes elevated after injury resulting in neuronal hyperexcitability and increased spasticity. We reported that stimulation with our non-invasive multi-site neuromodulation technology suppressed NKCC1 levels and reduced spasticity.

We describe herein that NKCC1 is elevated in SOD1-G93A mice, and that stimulation with our non-invasive multi-site neuromodulation technology results in reduction of elevated NKCC1 levels, thereby reducing the hyperexcitability of the neurons by normalizing chloride gradient. We further describe herein additional biochemical changes in spinal motor neurons following stimulation, as well as findings that stimulation results in reduction of tremor, slowing of disease progression, improvement of motor function, increased preservation of spinal motor neurons and increased survival in SOD1-G93A mice.

SUMMARY

In one or more embodiments, the present invention is directed to methods, devices and systems for treating amyotrophic lateral sclerosis and related disorders by applying a source of direct current (DC) to multiple locations along the neural axis in animals, including humans and other sentient beings. The locations for application of direct current include the spinal column, peripheral nerves and the cranium.

Our recent research has established important links between ALS and motor neuron hyperexcitability. We have developed a novel non-invasive approach that uses multi-site DCS (direct current stimulation), a form of non-invasive neuromodulation, to suppress hyperexcitable spinal motor neurons.

In international patent application, PCT/US2019/023675 (publication number WO2019/183536), filed 22 Mar. 2019, we disclose the first direct link between overexpression of a specific neuronal cotransporter (NKCC1) and the emergence of spasticity, another condition associated with motor neuron hyperexcitability. This Na—K—Cl cotransporter (NKCC1) is found on motor neurons and is involved in maintaining chloride gradient. We reported that our non-invasive intervention suppresses NKCC1 levels and reduces spasticity. The content of WO2019/183536 is hereby incorporated by reference into this application.

In international patent application, PCT/US2016/18167 (publication number WO2016/133960, we disclose application of our DCS-based intervention to the treatment of ALS. The content of WO2016/133960 is hereby incorporated by reference into this application.

We also published our human pilot study applying our non-invasive multi-site DCS approach to upper-limb spasticity in stroke and found significant reduction in spasticity and improvement in motor function that persisted for 5 weeks, and demonstrated safety (Paget-Blanc 2019).

In general, the present invention is directed to new methods, devices and systems for treatment of ALS and related disorders utilizing novel applications of multi-site DCS which incorporate trans-spinal direct current stimulation (tsDCS). The outcome is to suppress neuronal hyperexcitability and to reduce or prevent progression of the clinical manifestations of ALS. In particular, we have uncovered an entirely novel approach to slowing ALS progression using non-invasive neuromodulation in a manner that suppresses motor neuron hyperexcitability.

We have established a SOD1-G93A mouse colony and have been utilizing this transgenic ALS model for preclinical studies characterizing the effects of multi-site DCS. In SOD1-G93A mice treated non-invasively with our technology, we have shown reduction of tremor, slowing of disease progression, improvement of motor function, increased preservation of spinal motor neurons and increased survival.

We have found that NKCC1 is overexpressed, SOD1 is overexpressed, HSP70 is reduced, and phosphorylated tau is overexpressed in the SOD1-G93A model. We found that stimulation with anodal multi-site DCS results in suppression of NKCC1 at the intervention site. Furthermore, we found that stimulation with anodal multi-site DCS results in a decrease in SOD1, an increase in HSP70, upregulation of LCB3 expression and a decrease in phosphorylated tau in the spinal cord. Our novel invention is favorably applied to not only reduce ALS spasticity, but to slow ALS progression in humans.

This disclosure teaches an entirely new approach to treating and slowing ALS progression, preferably using non-invasive multi-site neuromodulation in a manner that suppresses motor neuron hyperexcitability.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In addition, the materials, methods, and examples are illustrative only and not intended to be limiting.

Where applicable or not specifically disclaimed, any one of the embodiments described herein are contemplated to be able to combine with any other one or more embodiments, even though the embodiments are described under different aspects of the disclosure.

These and other embodiments are disclosed and/or encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the disclosure solely to the specific embodiments described, may best be understood in conjunction with the accompanying drawings, in which FIG. 1A-1C show a set up for multi-site DCS stimulation in mice. FIG. 1A describes the stimulation setup where mice have three electrodes positioned along the spinal column, two sciatic nerve electrodes, and an abdominal return electrode. The rationale behind this electrode arrangement is to drive current across the spinal cord, and down the lower limbs. FIG. 1B shows the equivalent electrical circuit. FIG. 1C shows the mouse holder enabling mice to receive stimulation while permitting recording of muscle resistance and EMG.

FIG. 2A shows an animal in the mouse holder. FIG. 2B (top) shows the muscle resistance and EMG trace recorded before stimulation with anodal multi-site DCS. FIG. 2B (bottom) shows the muscle resistance and EMG trace recorded after 3 sessions of anodal multi-site DCS applied for 50 minutes per day.

FIGS. 3A-3B exhibit the immediate and last effects of anodal multi-site DCS on the EMG response to stretch in SOD1-G93A mice after disease onset. FIG. 3A shows the root-mean-square (green) and raw (pink) EMG traces obtained before and during stimulation with anodal multi-site DCS (1.5 mA at anode, positioned at T9-L6. EMG was recorded from the hind limb triceps surae). Increased muscle activity is visible in the EMG trace after disease onset. The high levels of activity are suppressed immediately at the start of stimulation, with decreased spike amplitude. FIG. 3B shows the root-mean-square (green) and raw (pink) EMG traces obtained after 3 days of stimulation with anodal multi-site DCS with each daily session lasting 50 minutes. The amplitude and frequency of EMG spikes are reduced even when stimulation is not being applied, suggesting lasting effects of the treatment.

FIG. 4 (top) shows tremors in the left hind paw as recorded using a micro-goniometer. FIG. 4 (middle) shows tremors in the right hind paw as recorded with a force transducer. FIG. 4 (bottom) shows the EMG trace of the tremors in the right hind limb triceps surae. In all three plots, the shaded area corresponds to before anodal multi-site DCS is applied. Tremors and spasms are suppressed immediately following start of stimulation on both sides. This enhancement is visible using all methods of measurement.

FIGS. 7A-7F display NKCC1 expression in spinal motor neurons following anodal multi-site DCS in SOD1-G93A mice. NKCC1 is a neuronal chloride co-transporter involved in the maintenance of chloride gradient. Overexpression of NKCC1 leads to hyperexcitability of the motor neurons. NKCC1 expression was evaluated using immunochemistry in non-carrier mice (FIG. 7A), non-stimulated carrier mice (FIG. 7B), stimulated carrier mice (FIG. 7C), and in the lumbar and cervical motor neurons of a same animal (FIGS. 7D and 7E). NKCC1 expression (in green) is increased in non-stimulated ALS mice as compared to non-carrier control mice and reduced by multi-site anodal DCS. In an animal receiving stimulation, NKCC1 expression is reduced underneath the site of the electrode (lumbar). FIG. 7F shows the relative expression levels of NKCC1 across the three groups.

FIGS. 8A-8F show reduced SOD1 expression in SOD1-G93A mice treated with anodal multi-site DCS. ALS mice overexpress mutant SOD1 (mSOD1) protein, leading to a pathological aggregation. FIGS. 8A-8E are photomicrographs of spinal cords of treated and untreated animals. FIG. 8F shows significantly lower mSDO1 expression in stimulated carrier animals as compared to non-stimulated carriers. N=control: 8 slices from 4 animals; stimulated: 5 slices from 5 animals.

FIG. 11 shows the effects of anodal multi-site DCS on the expression of LC3B in SOD1-G93A mice. LC3B is a protein marker for autophagy activity. The dysregulation of autophagy has been associated with ALS, and decreased LC3B could lead to accelerated motor neuron degeneration following abnormal accumulation of toxic proteins. LC3B expression is increased in carrier mice after stimulation as compared to non-stimulated carrier mice (control).

FIG. 15 shows an embodiment of a multi-channel unit to be used to sequentially treat ALS patients from the cervical spinal cord area to the lumbar spinal cord area to reduce spasticity and slow down disease progression. Each channel is limited to sourcing no more than 5 mA DC with a maximum current density of 0.56 mA/cm$^2$ for the smallest electrodes (below safety limits specified by applicable standards).

DETAILED DESCRIPTION

Figure 2A:
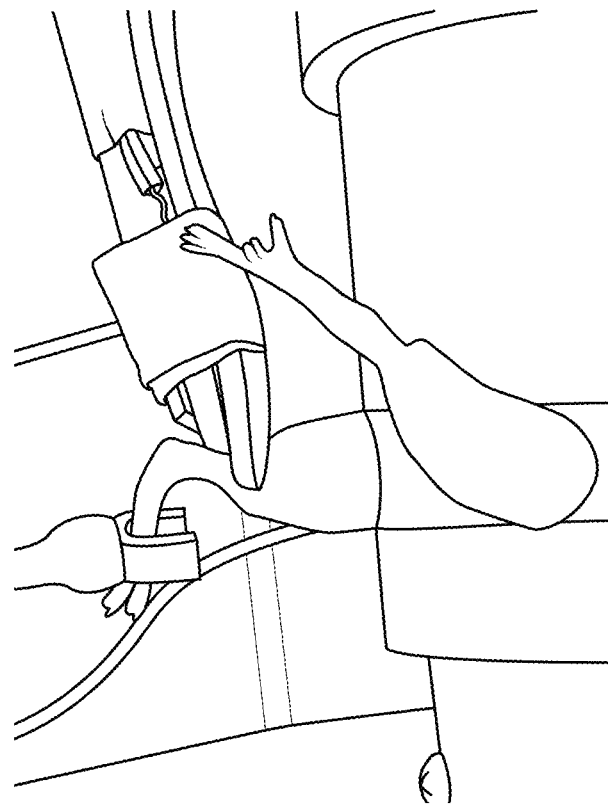
FIGS. 2A-2B depict the effects of 3 sessions of anodal DCS on muscle resistance and EMG response of the stretch reflex in SOD1-G93A mice.

The description is not to be taken in a limiting sense, but is made merely for the purpose of illustrating the general principles of these teachings, since the scope of these teachings is best defined by the appended claims.

The above illustrative and further embodiments are described below in conjunction with the following drawings, where specifically numbered components are described and will be appreciated to be thus described in all figures of the disclosure.

As used herein, the singular forms "a," "an," and "the" include the plural reference unless the context clearly dictates otherwise.

The term "stimulation," as used herein, refers to either excitation or inhibition of nerve fibers, also referred to as up regulation or down regulation.

The term "electrical stimulation," as used here in refers to the production or introduction of current into spinal nerve, neuron, circuit or pathway, whether by applying a voltage or magnetically inducing a current.

Direct Current Stimulation (DCS) is a non-invasive neuromodulation methodology that encompasses using direct current to treat diseases and disorders in mammal, in particular disease and disorders affecting the nervous system of vertebrate beings. DCS includes trans-spinal direct current stimulation (tsDCS), trans-cranial direct current stimulation (tcDCS) and trans-peripheral nerve direct current stimulation (tpnDCS).

Trans-spinal direct current stimulation (tsDCS) is a non-invasive neuromodulation methodology that uses direct current to modulate spinal cord neurons and spinal pathways. tsDCS can induce or suppress expression of specific proteins within the spinal cord neurons. The modulation of expression of specific proteins can impact the manifestations of conditions such as spasticity, hypertonia and dystonia, and can impact the progression of diseases linked to neuronal hyperexcitability.

According to embodiments of the invention, tsDCS includes stimulation of a target spinal location or locations. The stimulation includes applying direct current along a defined current path that includes the target spinal location or locations. The stimulation in one illustrative embodiment is substantially continuous and non-varying at subthreshold level. In another illustrative embodiment the stimulation is varying in whole or in part. In another illustrative embodiment the stimulation includes a combination of varying and non-varying stimulation. In another illustrative embodiment the stimulation includes pulses of stimulation. In yet another illustrative embodiment the stimulation includes pulses of continuous current stimulation where the current flow is not monodirectional.

Trans-cranial direct current stimulation (tcDCS) is a non-invasive neuromodulation methodology that uses direct current to modulate neurons and glial cells of the brain and cortical pathways. tcDCS can induce or suppress expression of specific proteins within neurons and other cells of the brain. The modulation of expression of specific proteins can be therapeutic for treating certain neurological diseases and disorders of the CNS including ALS, other motor neuron disorders and Alzheimer's disease.

According to embodiments of the invention, tcDCS includes stimulation of a target cranial location or locations. The stimulation includes applying direct current along a defined current path that includes the target cranial location or locations. The stimulation in one illustrative embodiment is substantially continuous and non-varying at subthreshold level. In another illustrative embodiment the stimulation is varying in whole or in part. In another illustrative embodiment the stimulation includes a combination of varying and non-varying stimulation. In another illustrative embodiment the stimulation includes pulses of stimulation. In yet another illustrative embodiment the stimulation includes pulses of continuous current stimulation where the current flow is not monodirectional.

Peripheral direct current stimulation (pDCS) is a non-invasive neuromodulation methodology that uses direct current to modulate peripheral nerves. pDCS can induce or suppress expression of specific proteins within the peripheral nerve and surrounding cells, and can affect the ability of the nerve to propagate descending and ascending signals. The modulation of expression of specific proteins can be used in the treatment of certain neurological disorders, including ALS and other motor neuron diseases.

According to embodiments of the invention, pDCS includes stimulation of a target peripheral nerve location or locations. The stimulation includes applying direct current along a defined current path that includes the target peripheral nerve location or locations. The stimulation in one illustrative embodiment is substantially continuous and non-varying at subthreshold level. In another illustrative embodiment the stimulation is varying in whole or in part. In another illustrative embodiment the stimulation includes a combination of varying and non-varying stimulation. In another illustrative embodiment the stimulation includes pulses of stimulation. In yet another illustrative embodiment the stimulation includes pulses of continuous current stimulation where the current flow is not monodirectional.

"Multi-site DCS" refers to the application of direct current stimulation simultaneously at multiple sites along the neural axis, which can include tsDCS, tcDCS and pDCS.

In practice of the invention, an electrode or array of electrodes is connected to a direct current source and placed at an area of interest, such as either directly over or near the dorsal aspect of the spinal cord, on the cranium or at or near a peripheral nerve. A return electrode or array of electrodes is placed distal therefrom to define a current flow path which in practice can be on the ventral aspect of the body, but not necessarily, directly opposite the electrode located at the area of interest. The direct current is applied to the treatment electrode located at the area of interest as either anode or cathode, depending upon function and desired stimulation.

The following terms may be understood, in the various illustrative by not limiting descriptions of embodiments of invention provided herein, to at least have the following definitions:

"Cathodal stimulation" refers to DCS where the cathode is placed at the desired area of interest for treatment.

"Anodal stimulation" refers to DCS where the anode is placed at the desired area of interest for treatment.

"Spasticity" is defined as the velocity-dependent overactivity of the stretch reflex. Thus, spasticity refers to a condition in which certain muscles are continuously or sporadically contracted. This contraction causes stiffness or tightness of the muscles and can interfere with normal movement, speech and gait, and can be painful. Spasticity is usually caused by damage to a region of the brain or spinal cord. The damage causes a change in the balance of signals between the nervous system and the muscles. This imbalance leads to increased activity in the muscles.

"Hypertonia" refers to impaired ability of damaged motor neurons to regulate descending pathways giving rise to disordered spinal reflexes, increased excitability of muscle spindles, and decreased synaptic inhibition. These consequences result in abnormally increased muscle tone of symptomatic muscles. Hypertonia includes patients exhibiting increased muscle tone in the absence of stretch reflex over-activity, thus distinguishing hypertonia from spasticity.

"Protein expression" refers to the level or amount of a protein or peptide contained within or produced by (e.g. excreted proteins or peptides) cells or tissues. "Differential expression", differential protein expression" and "differentially expressed" refer to a change in the level or amount of a protein or peptide contained within or produced by cells or tissues. Changes in protein expression can occur in response to specific external signals, such as chemical signals, mechanical signals or direct current stimulation. Such changes in expression can be an increase or a decrease in the level or amount of protein or peptide contained within or produced by cells or tissues. An increase in the level or amount of protein or peptide is also referred to as "up-regulation", and a decrease in the level or amount of protein or peptide is also referred to as "down-regulation".

"Messenger RNA expression" ("mRNA expression") refers to the level or amount of mRNA contained within cells or tissues. "Differential expression", "differential mRNA expression", "differential gene expression" and "differentially expressed" refer to a change in the level or amount of mRNA contained within cells or tissues. Changes in mRNA or gene expression can occur in response to specific external signals, such as chemical signals, mechanical signals or direct current stimulation. Such changes in expression can be an increase or a decrease in the level or amount of mRNA contained within cells or tissues. An increase in the level or amount of mRNA is also referred to as "up-regulation", and a decrease in the level or amount of mRNA is also referred to as "down-regulation". The terms "mRNA expression" and "gene expression" are used interchangeably throughout this disclosure.

Motor neuron diseases refer to certain neurological diseases that affect motor neurons and include amyotrophic lateral sclerosis, primary lateral sclerosis, progressive muscular atrophy, progressive bulbar palsy, spinal muscular atrophy and post-polio syndrome.

The present invention supports the hypothesis that the application of multi-site DCS can be beneficial in patients with ALS and other motor neuron diseases by both treating symptoms of the disease and slowing disease progression.

Na—K—Cl co-transporter isoform 1 (NKCC1) and K—Cl co-transporter isoform 2 (KCC2) are involved in establishing and maintaining the chloride ($Cl^-$) concentration gradient across nerve cell membranes (Misgeld et al., "The role of chloride transport in postsynaptic inhibition of hippocampal neurons", *Science*, 1986). Due to the importance of the electrochemical $Cl^-$ gradient in determining the strength of inhibition mediated by GAB A-A and glycine receptors, an imbalance in protein levels or the activities of NKCC1 and KCC2 has been predicted to lead to hyperexcitability and muscle dysfunction, particularly spasticity (Boulenguez et al., "Down-regulation of the potassium-chloride cotransporter KCC2 contributes to spasticity after spinal cord injury", *Nat. Med.*, 2010; Modol et al., "Prevention of NKCC1 phosphorylation avoids downregulation of KCC2 in central sensory pathways and reduces neuropathic pain after peripheral nerve injury", *Pain*, 2014). The mechanism of action underlying the long-term effects of direct current stimulation on spinal or brain excitability is largely unknown. It has been proposed that tsDCS can cause long-term changes in the excitability of spinal cord circuits (Ahmed, "Electrophysiological characterization of spino-sciatic and cortico-sciatic associative plasticity: modulation by trans-spinal direct current and effects on recovery after spinal cord injury in mice", *J. Neurosci.*, 2013; Ahmed, "Effects of cathodal trans-spinal direct current stimulation on lower urinary tract function in normal and spinal cord injury mice with overactive bladder", *J. Neural. Eng.*, 2017; Bolzoni and Jankowska, "Presynaptic and postsynaptic effects of local cathodal DC polarization within the spinal cord in anaesthetized animal preparations", *J. Physiol.*, 2015; Samaddar et al., "Transspinal direct current stimulation modulates migration and proliferation of adult newly born spinal cells in mice", *J. Appl. Physiol.*, 2016; Song et al., "Combined motor cortex and spinal cord neuromodulation promotes corticospinal system functional and structural plasticity and motor function after injury", *Exp. Neurol.*, 2016; Wieraszko and Ahmed, "Direct current-induced calcium trafficking in different neuronal preparations", *Neural. Plast.*, 2016). Our recent findings indicate that direct current stimulation can modulate the expression levels of certain proteins. Therefore, the present invention examined the effects of multi-site DCS that includes tsDCS on changes in protein expression of NKCC1, SOD1, HSP70, LCB3, tau in the spinal cord, as well as examined the effects of multi-site DCS on muscle EMG, tremor, motor function, motor neuron survival and survival of the animals.

A combination of electrophysiology, locomotor analysis and survival studies were used to reveal the influences of multi-site DCS on SOD1-G93A mice. In addition, quantitative real-time PCR (qPCR), Western blotting, and immunohistochemistry were performed to identify changes in protein and/or gene expression of NKCC1, SOD1, tau, HSP70 and LC3B in stimulated spinal tissue from mice.

Illustrative embodiments of the invention include treating motor neuron diseases or disorders or have been associated with elevated expression of NKCC1, SOD1 or tau. Representative examples of such diseases and disorders include amyotrophic lateral sclerosis, primary lateral sclerosis, progressive muscular atrophy, progressive bulbar palsy, spinal muscular atrophy, post-polio syndrome, Parkinson's disease, and Alzheimer's disease.

Illustrative embodiments of the invention include methods of treating ALS and other motor neuron diseases comprising the step of delivering non-invasive neuromodulation in a manner that decreases NKCC1 gene expression levels and/or protein expression levels, decreases SOD1 gene expression levels and/or protein expression levels, decreases tau gene expression levels and/or protein expression levels, or increases HSP70 gene expression levels and/or protein expression levels.

Illustrative embodiments of the invention include methods of treating a disorder in a vertebrate being, including the steps of: applying stimulation between a first electrode and a second electrode of a direct current source with the first electrode being at or proximate to a dorsal aspect of a spinal cord of a vertebrate being or with the first electrode being on a cranium of a vertebrate being; and applying the direct current stimulation at an intensity and for a period of time sufficient to change biological activity of or level of gene expression and/or protein expression of NKCC1, SOD1, HSP70, tau or LC3B; wherein the second electrode is placed at a position remote from the first electrode and the first and second electrodes are oppositely charged, and wherein the direct current is at least one of constant, continuous, pulsed, intermittent, varying and non-varying.

Illustrative embodiments of the invention include methods of treating a disorder in a vertebrate being that are double stimulation methods, including the steps of applying a first stimulation between a first electrode and a second electrode of a direct current source with the first electrode being at or proximate to a dorsal aspect of a spinal cord of a vertebrate being; applying a second stimulation between a third electrode and a fourth electrode of a direct current source with one of the third electrode being at or proximate to a peripheral nerve of a vertebrate being; and applying the direct current stimulation at an intensity and for a period of time sufficient to change biological activity of or level of gene expression and/or protein expression of NKCC1, SOD1, HSP70, tau or LC3B; wherein the second electrode is placed at a position remote from the first electrode and the first and second electrodes are oppositely charged, and the fourth electrode is placed at a position remote from the third electrodes and the third and fourth electrodes are oppositely charged, and wherein the direct current is at least one of constant, continuous, pulsed, intermittent, varying and non-varying.

In some embodiments of the double stimulation method, the first and second stimulations are applied simultaneously or sequentially.

Illustrative embodiments of the invention include methods of treating a disorder in a vertebrate being that are triple stimulation methods, including the steps of applying a first stimulation between a first electrode and a second electrode of a direct current source with the first electrode being at or proximate to a dorsal aspect of a spinal cord of a vertebrate being; applying a second stimulation between a third electrode and a fourth electrode of a direct current source with one of the third electrode being at or proximate to a peripheral nerve of a vertebrate being; and applying the direct current stimulation at an intensity and for a period of time sufficient to change biological activity of or level of gene expression and/or protein expression of NKCC1, SOD1, HSP70, tau or LC3B; wherein the second electrode is placed at a position remote from the first electrode and the first and second electrodes are oppositely charged, and the fourth electrode is placed at a position remote from the third electrodes and the third and fourth electrodes are oppositely charged, and wherein the direct current is at least one of constant, continuous, pulsed, intermittent, varying and non-varying; and further comprising applying a third stimulation between a fifth electrode and a sixth electrode of a direct current source with the fifth electrode being on a cranium of a vertebrate being; and wherein the sixth electrode is placed at a position remote from the fifth electrode and the fifth and sixth electrodes are oppositely charged.

In some embodiments, of the triple stimulation method the first, second and third stimulations are applied simultaneously or sequentially.

In illustrative examples of the invention where peripheral nerves are stimulated, the peripheral nerve innervates a skeletal muscle. Representative examples of some peripheral nerves include leg nerves or arm nerves including, but not limited to a sciatic nerve, a peroneal nerve, a plantar digital nerve, a femoral nerve, a saphenous nerve, a sural nerve, a tibial nerve, a median nerve, a musculocutaneous nerve, a palmar digital nerve, a radial nerve, and an ulnar nerve.

In some embodiments of the single, double and triple stimulation methods, the stimulations are performed over a period of time that includes a series of stimulation sessions on 1 or more days, the days being consecutive or non-consecutive.

In some embodiments of the single, double and triple stimulation methods, the disorder being treated is a muscle tone disorder such as spasticity, spasticity following spinal cord injury, hypertonia and dystonia.

In some embodiments of the single, double and triple stimulation methods, the biological activity of or the level of gene expression and/or protein expression of NKCC1 is decreased, the biological activity of or the level of gene expression and/or protein expression of SOD1 is decreased, the biological activity of or the level of gene expression and/or protein expression of tau is decreased, the biological activity of or the level of gene expression and/or protein expression of HSP70 is increased, or the biological activity of or the level of gene expression and/or protein expression of LC3B is decreased.

Illustrative embodiments of the invention include methods of treating ALS in a vertebrate being. The non-invasive electrical stimulation methods described herein are designed to halt the progression of ALS by protecting motor and cortical neurons from dying, i.e. the methods described herein prolong neuronal cell life or at least slow down the rate of motor and cortical neuron cell death. Without intending to be bound by theory, it is believed that either suppressing NKCC, SOD1 or tau expression and/or activity, or increasing HSP70 or LC3B expression and/or activity in spinal and cortical neurons will lead to a halt in the progression of ALS by prolonging motor and cortical neuronal cell life.

In some embodiments, the methods of treating ALS include the steps of: applying stimulation between an A electrode and a B electrode of a direct current source with the A electrode being at or proximate to a dorsal aspect of a spinal cord of a vertebrate being or with the A electrode being on a cranium of a vertebrate being; and applying the direct current stimulation at an intensity and for a period of time sufficient to prolong neuronal cell life associated with ALS disease state; wherein the B electrode is placed at a position remote from the A electrode and the A and B electrodes are oppositely charged, and wherein the direct current is at least one of constant, continuous, pulsed, intermittent, varying and non-varying.

It is envisioned that, when treating ALS patients, multiple spinal cord locations along the length of the spinal cord will be treated in order to prolong neuronal cell life at multiple locations. Accordingly, in some embodiments, the methods of treating ALS include a plurality of A electrodes located at or proximate to a plurality of positions along the dorsal aspect of the spinal cord and a plurality of B electrodes placed at positions remote from the plurality of A electrodes. In other embodiments, one set of A and B electrodes is used, and the electrodes are moved to different locations along the length of the spinal cord in a series of treatments.

It is also envisioned that, when treating ALS patients, multiple regions of the brain associated with movement control will be treated including the motor cortex (Area 6 and Area 4, also known as the primary motor cortex), basal ganglia and the cerebellum. Accordingly, in some embodiments, the methods of treating ALS include a plurality of A electrodes located at a plurality of positions on the cranium associated with movement control and a plurality of B electrodes are placed at positions remote from the plurality of A electrodes. In other embodiments, one set of A and B electrodes is used, and the electrodes are moved to different cranial positions associated with movement control in a series of treatments.

In some embodiments of the methods of treating ALS, the stimulation applied between the plurality of A and B electrodes is applied simultaneously or sequentially.

In some embodiments, the methods of treating ALS patients include the steps of: applying a first stimulation between an A electrode and a B electrode of a direct current source with the A electrode being at or proximate to a dorsal aspect of a spinal cord of a vertebrate being; applying a second stimulation between a C electrode and a D electrode of a direct current source with the C electrode being on a cranium of a vertebrate being; and applying the direct current stimulation at an intensity and for a period of time sufficient to prolong neuronal cell life; wherein the B electrode is placed at a position remote from the A electrode and the A and B electrodes are oppositely charged, and the D electrode is placed at a position remote from the C electrode and the C and D electrodes are oppositely charged, and wherein the direct current is constant or pulsed. In some embodiments, the first and second stimulations are applied simultaneously or sequentially.

In some embodiments, the methods of treating ALS include a plurality of A electrodes located at or proximate to a plurality of positions along the dorsal aspect of the spinal cord and a plurality of B electrodes placed at positions remote from the plurality of A electrodes. In other embodiments, one set of A and B electrodes is used, and the electrodes are moved to different locations along the length of the spinal cord in a series of treatments.

In some embodiments, the methods of treating ALS include a plurality of C electrodes located at a plurality of positions on the cranium associated with movement control and a plurality of D electrodes are placed at positions remote from the plurality of C electrodes. In other embodiments, one set of C and D electrodes is used, and the electrodes are moved to different cranial positions associated with movement control in a series of treatments.

In some embodiments, the stimulation applied between the plurality of A and B electrodes and between the plurality of C and D electrodes is applied simultaneously or sequentially.

In some embodiments, the methods of treating ALS further include applying a third stimulation between an E electrode and an F electrode of a direct current source with the E electrode being at or proximate to a peripheral nerve of a vertebrate being; and wherein the F electrode is placed at a position remote from the E electrode and the E and F electrodes are oppositely charged. In some embodiments the first, second and third stimulations are applied simultaneously or sequentially.

In some embodiments, the methods of treating ALS include a plurality of E electrodes located at or proximate to a plurality of positions along a peripheral nerve or are located at or proximate to a plurality of peripheral nerves and a plurality of F electrodes are placed at positions remote from the plurality of E electrodes. In other embodiments, one set of C and D electrodes is used, and the electrodes are moved to different positions along a peripheral nerve or are moved to different peripheral nerves. In some embodiments, the stimulation applied between the plurality of E and F electrodes is applied simultaneously or sequentially. In some embodiments where peripheral nerves are stimulated, the peripheral nerve innervates a skeletal muscle. Representative examples of some peripheral nerves are disclosed above.

In some embodiments of the methods of treating ALS, the period of time comprises a series of stimulation sessions on 1 or more days, the days being consecutive or non-consecutive.

In some embodiments of the methods of treating ALS, the method includes applying the direct current stimulation at an intensity and for a period of time sufficient to change biological activity of or level of gene expression and/or protein expression of NKCC1, SOD1, tau, HSP70 or LC3B. In some embodiments, the biological activity of or the level of gene expression and/or protein expression of NKCC1, SOD1 or tau is decreased, while in other embodiments, the biological activity of or the level of gene expression and/or protein expression of HSP70 or LC3B is increased.

In some embodiments, we use multiple spinal electrodes (e.g., anode) each with its own constant current source. This divides the current and delivers more even stimulation as compared to one large rectangular spinal electrode.

In other embodiments, multiple spinal electrodes (e.g., anode) each with its own constant current source, are combined with a capability for bilateral peripheral stimulation by using additional constant current sources.

In another embodiment we also include simultaneous cortical stimulation.

In practices of embodiments of the invention, cervical and lumbar stimulation treatments are conducted on different days, e.g., upper limbs on one day, lower limbs the following day.

Animals, particularly mammals including humans, are the subjects of the DCS treatments discussed herein. In illustrative and non-limiting embodiments, treatment of humans in practice of the invention can include application of DCS, for example, generally within a range of over 1 mA and under 6 mA, and more particularly within a range of about 3.5-4 mA, and can be applied for about 20-60 min/day. In other illustrative and non-limiting embodiments, treatments of humans in practice of the invention can include application of trans-cranial DCS (tcDCS) or peripheral DCS (pDCS). DCS treatment can be as often as indicated on a scheduled day or alternating days, or any other treatment regime intended to affect repair or recovery.

In practicing the methods of the invention disclosed herein, the following systems or devices are used.

Illustrative embodiments of the invention include a system for treatment of ALS or other motor neuron diseases in a vertebrate being, the system including: a first stimulation component configured to provide peripheral direct current stimulation of a peripheral nerve associated with motor neuron disease in a vertebrate being; the first stimulation component including a neural stimulation circuit having neural stimulation poles configured to stimulate said peripheral nerve; a second stimulation component configured to provide spinal direct current stimulation at a spinal location associated with regulation of said peripheral nerve, said second stimulation component defining a spinal stimulation circuit having an active spinal stimulation pole and a spinal reference pole, said spinal stimulation circuit configured to provide constant-current trans-spinal direct current stimulation between said spinal stimulation pole and said spinal reference pole for stimulating said spinal location; the active spinal stimulation pole being relatively proximal to said spinal location; the spinal reference pole being relatively distal to said spinal location; and a controller component configured to ensure that said active spinal pole and said proximal neural pole are excited at opposite polarities, forming a resulting polarization circuit, said resulting polarization circuit being configured to provide a polarizing current flow between said active spinal pole and said proximal neural pole according to said opposite polarities, for changing biological activity of or level of gene expression and/or protein expression of a target molecule according to said polarizing current flow; said controller component being also configured to provide peripheral direct current stimulation and spinal direct current stimulation for a predetermined time period and repeat stimulation a predetermined number of times over a predetermined number of days.

In some embodiments of the system, the controller component is configured to provide said current flow including at least one of constant, continuous, pulsed, intermittent, varying and non-varying current flow.

In some embodiments of the system, the controller component is further configured to simultaneously control the range of current supplied by the first and second stimulation components.

In some embodiments of the system, the first stimulation component includes positive and negative poles for providing stimulation current to stimulation electrodes disposed for stimulation of said peripheral nerve, said positive and negative poles disposed for one electrode operatively connected to the positive pole and another electrode operatively connected to the negative pole. In some embodiments of the system, the second stimulation component includes positive and negative poles for providing stimulation current to stimulation electrodes disposed for delivering stimulation across said spinal location, said positive and negative poles disposed for one electrode operatively connected to the positive pole and another electrode operatively connected to the negative pole.

In some embodiments of the system, at least one of the stimulation electrodes is implanted.

In yet other embodiments of the system, at least one of the controller component and an electrical source are disposed in a wearable housing.

In some embodiments of the system, the predetermined time period, the predetermined number of times and the predetermined number of days are selected to change biological activity of or level of gene expression and/or protein expression of NKCC1, SOD1, tau, HSP70 or LC3B. In certain embodiments of the system, the biological activity of or the level of gene expression and/or protein expression of NKCC1, SOD1 or tau is decreased, while other embodiments, the biological activity of or the level of gene expression and/or protein expression of HSP70 or LC3B is increased.

Illustrative embodiments of the invention include a stimulation device for regulating biological activity associated with one of the spinal cord or the brain, comprising: a direct current voltage source having a plurality of terminals; a first of the terminals for connecting a first electrode to the direct current voltage source; the first electrode being at one of a dorsal aspect of a spinal cord of a vertebrate being or on a cranium of a vertebrate being; a second of the terminals for connecting a second electrode to the direct current voltage source; the second electrode being placed at a position remote from the first electrode; the first and second electrodes being oppositely charged; and a controller component configured to control of current flow between the electrodes; the controller component being also configured to provide direct current stimulation for a predetermined time period and repeat stimulation a predetermined number of times over a predetermined number of days.

In some embodiments of the stimulation device, the controller component is configured to provide said current flow including at least one of constant, continuous, pulsed, intermittent, varying, and non-varying current flow.

In some embodiments of the stimulation device, at least one of the first and second electrodes is implanted.

In yet other embodiments of the stimulation device, at least one of the controller component and the direct current voltage source are disposed in a wearable housing.

In some embodiments of the stimulation device, the predetermined time period, the predetermined number of times and the predetermined number of days are selected to change biological activity of or level of gene expression and/or protein expression of NKCC1, SOD1, tau, HSP70 or LC3B.

Illustrative embodiments of the invention include systems for treatment of ALS in a vertebrate being, the system including: a plurality of A stimulation components configured to provide peripheral direct current stimulation of a peripheral nerve at a plurality of locations along the peripheral nerve or to provide peripheral direct current stimulation of a plurality of peripheral nerves in a vertebrate being; each of said A stimulation components including a neural stimulation circuit having neural stimulation poles configured to stimulate said peripheral nerve or plurality of peripheral nerves; a plurality of B stimulation components configured to provide spinal direct current stimulation at a plurality of spinal locations associated with regulation of said peripheral nerve or plurality of peripheral nerves, each of said B stimulation components defining a spinal stimulation circuit having an active spinal stimulation pole and a spinal reference pole, said spinal stimulation circuit configured to provide constant-current trans-spinal direct current stimulation between said spinal stimulation pole and said spinal reference pole for stimulating said spinal location; the active spinal stimulation pole being relatively proximal to said spinal location; the spinal reference pole being relatively distal to said spinal location; and a controller component configured to ensure that said active spinal pole and said proximal neural pole are excited at opposite polarities, forming a resulting polarization circuit, said resulting polarization circuit being configured to provide a polarizing current flow between said active spinal pole and said proximal neural pole according to said opposite polarities, for changing biological activity of or level of gene expression and/or protein expression of a target molecule according to said polarizing current flow; said controller component being also configured to provide peripheral direct current stimulation and spinal direct current stimulation for a predetermined time period and repeat stimulation a predetermined number of times over a predetermined number of days.

In some embodiments of the system, the controller component is configured to provide said current flow including at least one of constant, continuous, pulsed, intermittent, varying and non-varying current flow.

In some embodiments of the system, the controller component is further configured to simultaneously control the range of current supplied by the A and B stimulation components.

In some embodiments of the system, the A stimulation components include positive and negative poles for providing stimulation current to stimulation electrodes disposed for stimulation of said plurality of locations of a peripheral nerve or said plurality of peripheral nerves, said positive and negative poles disposed for one electrode operatively connected to the positive pole and another electrode operatively connected to the negative pole.

In some embodiments of the system, the B stimulation components include positive and negative poles for providing stimulation current to stimulation electrodes disposed for delivering stimulation across said plurality of spinal locations, said positive and negative poles disposed for one electrode operatively connected to the positive pole and another electrode operatively connected to the negative pole.

In some embodiments of the system, at least one of the stimulation electrodes is implanted.

In yet other embodiments of the system, at least one of the controller component and an electrical source are disposed in a wearable housing.

In some embodiments of the system, the predetermined time period, the predetermined number of times and the predetermined number of days are selected to change biological activity of or level of gene expression and/or protein expression of NKCC1, SOD1, tau, HSP70 or LC3B. In certain embodiments of the system, the biological activity of or the level of gene expression and/or protein expression of NKCC1, SOD1, or tau is decreased. In certain embodiments of the system, the biological activity of or the level of gene expression and/or protein expression of HSP70 or LC3B is increased.

Illustrative embodiments of the invention include a stimulation device for treatment of ALS, comprising: a direct current voltage source having a plurality of terminals; a plurality of A terminals for connecting a plurality of A electrodes to the direct current voltage source; the plurality of A electrodes being at a plurality of locations of a dorsal aspect of a spinal cord of a vertebrate being or at a plurality of locations on a cranium of a vertebrate being; a plurality of B terminals for connecting a plurality of B electrodes to the direct current voltage source; the plurality of B electrodes being placed positions remote from the plurality of A electrodes; the A and B electrodes being oppositely charged; and a controller component configured to control of current flow between the electrodes; the controller component being also configured to provide direct current stimulation for a predetermined time period and repeat stimulation a predetermined number of times over a predetermined number of days.

In some embodiments of the stimulation device, the controller component is configured to provide said current flow including at least one of constant, continuous, pulsed, intermittent, varying, and non-varying current flow.

In some embodiments of the stimulation device, at least one of the A and B electrodes is implanted.

In yet other embodiments of the stimulation device, at least one of the controller component and the direct current voltage source are disposed in a wearable housing.

In some embodiments of the stimulation device, the predetermined time period, the predetermined number of times and the predetermined number of days are selected to change biological activity of or level of gene expression and/or protein expression of NKCC1, SOD1, tau, HSP70 or LC3B. In some embodiments of the stimulation device, the biological activity of or the level of gene expression and/or protein expression of NKCC1, SOD1 or tau is decreased. In some embodiments of the stimulation device, the biological activity of or the level of gene expression and/or protein expression of HSP70 or LC3B is increased.

The systems and stimulation devices of the present invention are further described below with reference to the figures.

Although the above described embodiments illustrate a pair of electrodes being applied by each stimulation components, embodiments in which a plurality of pair of electrodes are applied with one stimulation component are also within the scope of these teachings. For example, in some embodiments, a plurality of pair of electrodes are applied with the first stimulation component, where one of each pair of electrodes is applied to a different spinal or cranial location.

While these teachings have been described in terms of specific embodiments, it is evident in view of the foregoing description that numerous alternatives, modifications and variations will be apparent to those skilled in the art. Accordingly, these teachings are intended to encompass all such alternatives, modifications and variations which fall within the scope and spirit of the present teachings and the following claims.

EXAMPLES

Example 1: Materials and Methods

Animals

Transgenic SOD1-G93A mice were used for all of the animal studies performed from a breeding colony established at CUNY/CSI. The transgenic SOD1-G93A mouse is the most widely-used murine model of ALS and is engineered to overexpress a mutant form of human Cu/Zn superoxide dismutase 1 (SOD1). The mice develop muscle tremors, paralysis, premature death and exhibit motor neuron loss. Mice are assigned to specific group based on genotyping and copy number at 60 days of age (presymptomatic). qPCR is used to quantify the number of copies in carrier animals. The inclusion of female and male groups is based on publications which found that female and male mice (G93A) have different survival rates. For therapeutic stimulation experiments, carrier animals were divided into 2 groups: 1) Anodal multi-site DCS-treated group; and 2) Carrier unstimulated group. Treatment starts on the first day of confirmed disease and signs of motor dysfunction (early stage). This is confirmed using a grid walking test. Animals are allowed to walk 30 steps and videotaped from the underside. Videos were analyzed by a blinded investigator. We used a 6-point foot fault score system to quantify the grid walking. Since grid walking is very sensitive to spinal or cortical dysfunction (Ruegsegger, "Aberrant association of misfolded SOD1 with Na(+)/K(+)ATPase-α3 impairs its activity and contributes to motor neuron vulnerability in ALS", Acta. Neuropathol., 2016), this system was found to be very accurate in detecting early stages of disease in mice (preliminary data). All of the study protocols were approved by the College of Staten Island IACUC committee.

Circuit and Power Source

Passing current to peripheral nerves is required to attenuate and modulate motor neuron hyperexcitability (Ahmed, "Trans-spinal direct current stimulation modifies spinal cord excitability through synaptic and axonal mechanisms", Physiol. Rep., 2014). Moreover, the direction and distribution of this current can be regulated (Ahmed, "Effects of cathodal trans-spinal direct current stimulation on lower urinary tract function in normal and spinal cord injury mice with overactive bladder", J. Neural. Eng., 2017). The multi-site DCS protocols of the present study required a modification of the trans-spinal circuit that was originally designed in our laboratory to be used with anesthetized animals (Ahmed, "Trans-spinal direct current stimulation alters muscle tone in mice with and without spinal cord injury with spasticity", J. Neurosci., 2014). Briefly, the circuit was modified to non-invasively pass direct current (DC) to the spinal cord and the sciatic nerves of the affected limbs by using over-skin electrodes as shown in FIG. 1A. The reference current source delivered the spinal current divided through three spinal electrodes. To prevent evoking nerve activity, the current passing from the spinal electrodes through to the sciatic nerve electrodes was attenuated by dividing the spinal current into three branches: the first branch connected directly to the abdominal electrode and carried un-attenuated current, while the second and third branches passed through 300 kΩ resistors to attenuate current to the sciatic nerves. A schematic of the circuit is shown in FIG. 1B. Current was supplied by a GRASS stimulator with a dedicated DC unit (S88, GRASS Technologies/NATUS). Monitoring of current parameters and verification of DC attenuation was performed at the beginning, during, and upon completion of each experiment by using a bench-top digital multi-meter (34401A, Agilent/Keysight Technologies, CA USA).

Mouse Holder

A mouse restraining system was fabricated in our laboratory (FIG. 1C) from three components. 1) A clear Plexiglas acrylic tube served as the mouse holding chamber. 2) An internally adjustable support system made of a clear acrylic concave stabilization plate. The location of the plate was able to be adjusted linearly along the length of the chamber via a handle that protruded through a cutout that ran the entire length of the tube. In addition, the concave surface of the plate was designed to contour to the back of the animal, thereby securing it dorsally. This surface could also be adjusted externally to accommodate various sizes of mice. 3) Four over-skin stimulating electrodes with each composed of a wick-covered 1 cm×1.5 cm stainless-steel plate. One of the electrodes was permanently fixed to the floor of the holding chamber (for the abdominal reference electrode), while a second electrode was permanently fixed to the middle of the stabilization plate (for the dorsal active spinal electrode) and the location of this plate could be adjusted. The remaining two electrodes could be adjusted linearly by sliding them along cutouts present on the long sides of the stabilization plate, and these served as left and right sciatic nerve conductors, respectively. The abdominal surface of the holding chamber had two openings, one for each of the animal's hind limbs. Each opening was equipped with a knee stabilizer pad to ensure full knee extension during testing. Prior to testing, a cap with an opening in the center was placed on the anterior end of the holding chamber for breathing and for isoflurane administration. To limit hind limb movement to the ankle joint during stretching, another acrylic stand was created to secure the distal leg. The stand had an adjustable stainless-steel ankle stabilizer clamp that could be moved in the x, y, and z axes to achieve proper alignment of the foot under the presser, and to adjust the hip angle of the animal before stretching.

Example 2: Anodal Multi-Site DCS Results in Suppression of EMG Activity

Figure 2B:
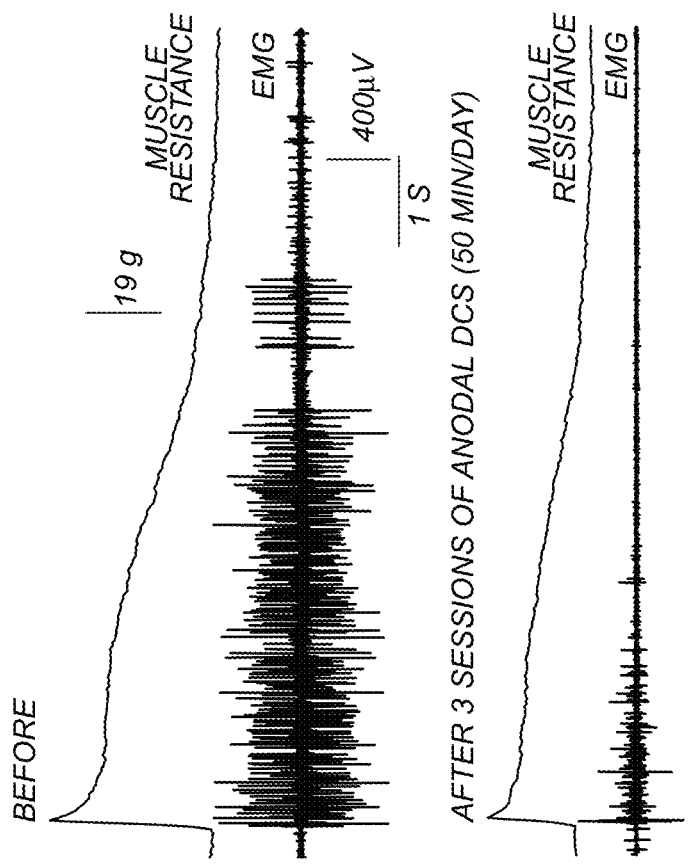

The immediate and lasting effects of anodal multi-site DCS on the EMG response to stretch in SOD1-G93A mice after disease onset is shown in FIGS. 2A-2B and 3A-3B. FIGS. 2A-2B depict the effects of 3 sessions of anodal DCS on muscle resistance and EMG response of the stretch reflex in SOD1-G93A mice. FIG. 2A shows an animal in the mouse holder. FIG. 2B (top) shows the muscle resistance and EMG trace recorded before stimulation with anodal multi-site DCS (1.5 mA). FIG. 2B (bottom) shows the muscle resistance and EMG trace recorded after 3 sessions of anodal multi-site DCS applied for 50 minutes per day. FIG. 3A shows the root-mean-square (green) and raw (pink) EMG traces obtained before and during stimulation with anodal multi-site DCS (1.5 mA at anode, positioned at T9-L6. EMG was recorded from the hind limb triceps surae). Increased muscle activity is visible in the EMG trace after disease onset. The high levels of activity are suppressed immediately at the start of stimulation, with decreased spike amplitude. FIG. 3B shows the root-mean-square (green) and raw (pink) EMG traces obtained after 3 days of stimulation with anodal multi-site DCS with each daily session lasting 50 minutes. The amplitude and frequency of EMG spikes are reduced even when stimulation is not being applied, suggesting lasting effects of the treatment.

Example 3: Anodal Multi-Site DCS Results in Suppression of Tremors

Figure 4:
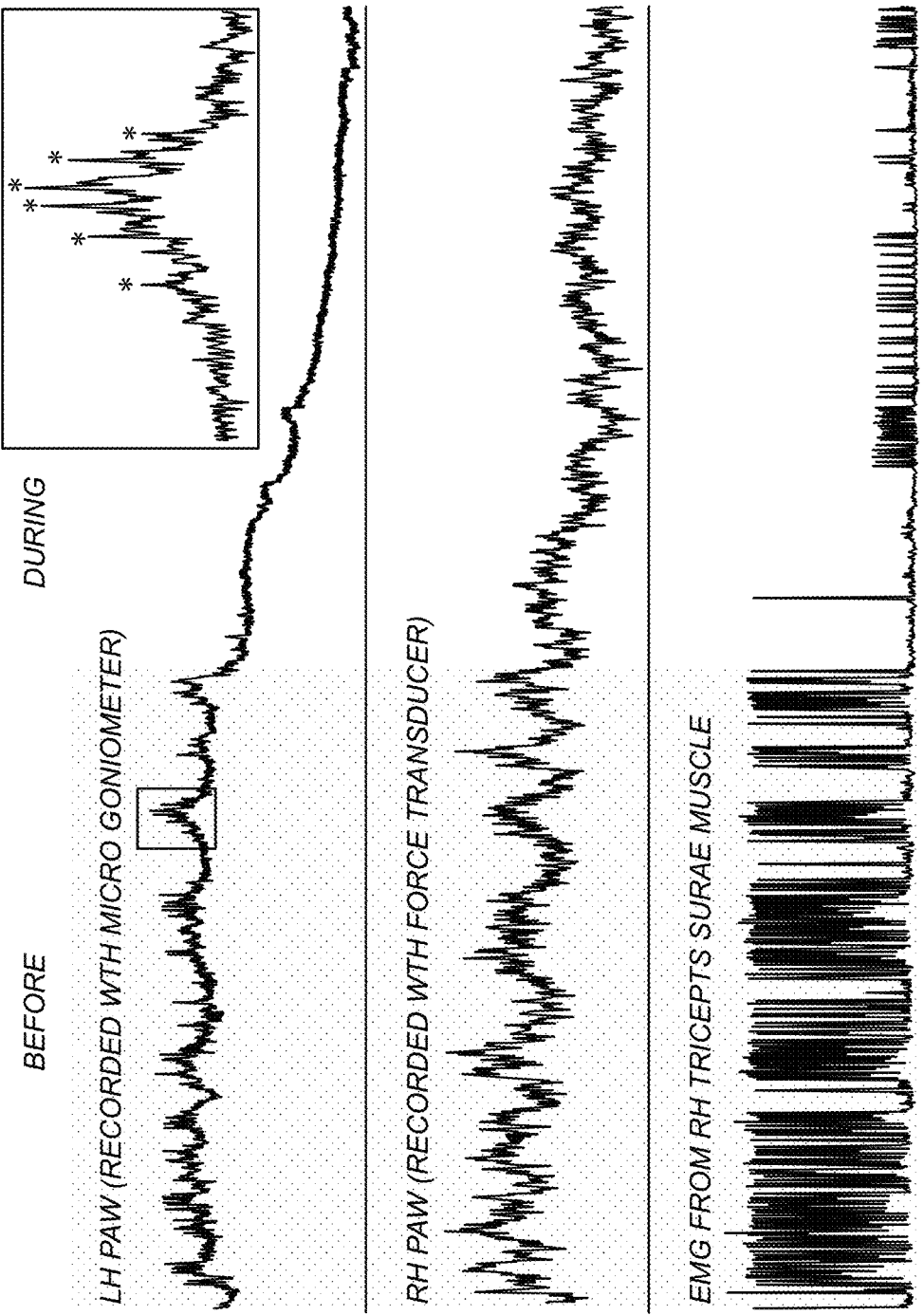
FIG. 4 show the immediate effects of anodal multi-site DCS on tremors in the hind limbs of SOD1-G93A mice. ALS mice display tremors and spasms after symptom onset. These tremors can be measured using either a micro-goniometer or a force transducer.
Figure 5:
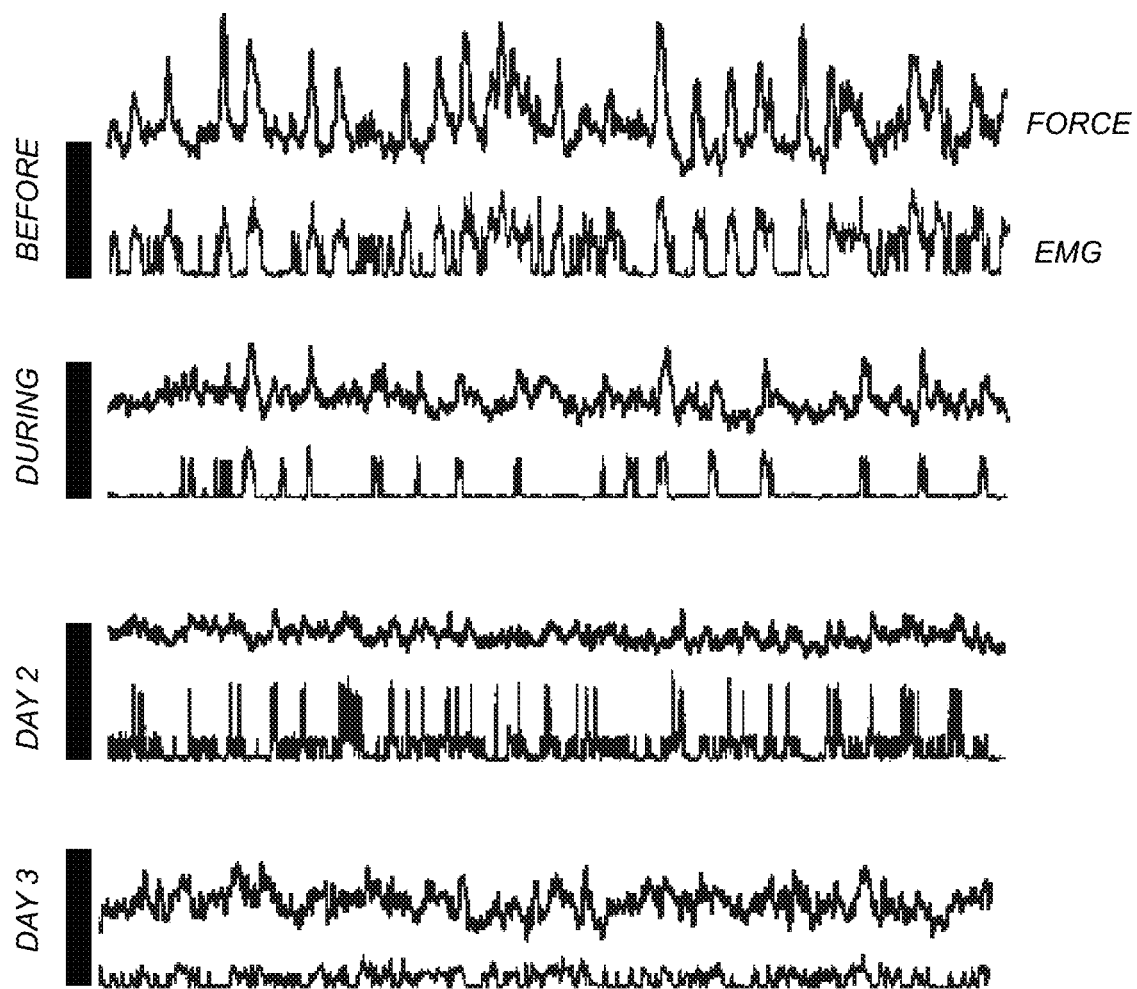
FIG. 5 displays the lasting effects of anodal multi-site DCS on involuntary muscle contractions and tremors in SOD1-G93A mice after symptom onset. From top to bottom, the figure shows the EMG trace (in blue) and force measurement (in black, recorded with a force transducer), measured before stimulation, during stimulation, after 2 days of stimulation and after 3 days of stimulation. The tremors are immediately suppressed during stimulation. The activity measured after two days of stimulation shows additional reduction of tremors. After 3 days of stimulation, the tremors and muscle spasms are further reduced even without stimulation.

ALS mice display tremors and spasms after symptom onset. These tremors can be measured using either a micro-goniometer or a force transducer. FIG. 4 show the immediate effects of anodal multi-site DCS on tremors in the hind limbs of SOD1-G93A mice. FIG. 4 (top) shows tremors in the left hind paw as recorded using a micro-goniometer. FIG. 4 (middle) shows tremors in the right hind paw as recorded with a force transducer. FIG. 4 (bottom) shows the EMG trace of the tremors in the right hind limb triceps surae. In all three plots, the shaded area corresponds to before anodal multi-site DCS is applied. Tremors and spasms are suppressed immediately following start of stimulation on both sides. This enhancement is visible using all methods of measurement. FIG. 5 displays the lasting effects of anodal multi-site DCS on involuntary muscle contractions and tremors in SOD1-G93A mice after symptom onset. From top to bottom, the figure shows the EMG trace (in blue) and force measurement (in black, recorded with a force transducer), measured before stimulation, during stimulation, after 2 days of stimulation and after 3 days of stimulation. The tremors are immediately suppressed during stimulation. The activity measured after two days of stimulation shows additional reduction of tremors. After 3 days of stimulation, the tremors and muscle spasms are further reduced even without stimulation.

Example 4: Anodal Multi-Site DCS Results in Improvement of Motor Function

Figure 6:
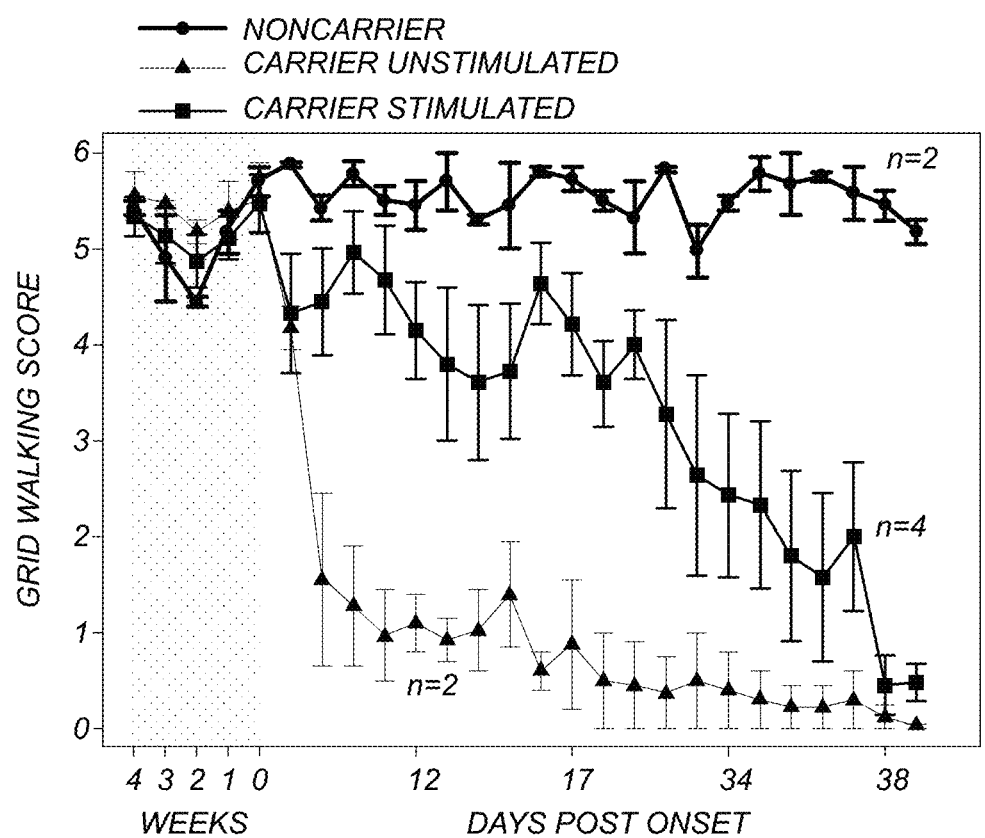
FIG. 6 shows improvements in motor function in SOD1-G93A mice following anodal multi-site DCS. Motor function was evaluated using a modified horizontal ladder scoring system, with a scoring scale of 0-6 (6 is perfect score, with mid-portion of palm of a limb is placed on a rung to bear the animal's full weight) in stimulated and non-stimulated carrier mice as well as non-carrier mice. Mice were video-recorded from below with videos stored and analyzed by investigators blinded to mice treatment. Mice received stimulation for 1 hour per day for 2 days per week, with 1.5 mA delivered through the spinal anode. Stimulation started after disease onset, on average at 106 days of age in this group. Grid walking scores of non-stimulated ALS mice rapidly decline after disease onset (blue), as compared to non-carrier controls (black). In stimulated carrier mice (red), the grid walking scores are significantly higher than scores of unstimulated carrier mice, reflecting enhanced preservation of motor function following stimulation. N=2 non-carriers, 4 stimulated carriers, 2 non-stimulated carriers. Data are presented as mean±SEM.

Motor function was evaluated using a modified horizontal ladder scoring system, with a scoring scale of 0-6 (6 is perfect score, with mid-portion of palm of mouse limb placed on a rung to bear the animal's full weight) in stimulated and non-stimulated carrier mice as well as non-carrier mice. Mice were video-recorded from below with videos stored and analyzed by investigators blinded to mice treatment. FIG. 6 shows improvements in motor function in SOD1-G93A mice following anodal multi-site DCS. Mice received stimulation for 1 hour per day for 2 days per week, with 1.5 mA delivered through the spinal anode. Stimulation started after disease onset, on average at 106 days of age in this group. Grid walking scores of non-stimulated ALS mice rapidly decline after disease onset (blue), as compared to non-carrier controls (black). In stimulated carrier mice (red), the grid walking scores are significantly higher than scores of unstimulated carrier mice, reflecting enhanced preservation of motor function following stimulation. N=2 non-carriers, 4 stimulated carriers, 2 non-stimulated carriers. Data are presented as mean±SEM.

Example 5: Anodal Multi-Site DCS Reduces Expression of NKCC1

NKCC1 is a neuronal chloride co-transporter involved in the maintenance of chloride gradient. Overexpression of NKCC1 leads to hyperexcitability of the motor neurons. FIGS. 7A-7F display NKCC1 expression in spinal motor neurons following anodal multi-site DCS in SOD1-G93A mice. NKCC1 expression was evaluated using immunochemistry in non-carrier mice (FIG. 7A), non-stimulated carrier mice (FIG. 7B), stimulated carrier mice (FIG. 7C), and in the lumbar and cervical motor neurons of a same animal (FIGS. 7D and 7E). NKCC1 expression (in green) is increased in non-stimulated ALS mice as compared to non-carrier control mice and reduced by multi-site anodal DCS. In an animal receiving stimulation, NKCC1 expression is reduced underneath the site of the electrode (lumbar). FIG. 7F shows the relative expression levels of NKCC1 across the three groups.
Western Blot Spinal cord tissues were collected and immediately placed in dry ice. The samples were subsequently homogenized in RIPA buffer (Cat. #: BP-115, Boston Bio Products, Ashland, MA, USA) containing a Protease Inhibitor Cocktail (SC-29131, Santa Cruz Biotechnology Dallas Texas, U.S.A.), Phosphatase Inhibitors Cocktail 11 (Cat. #: BP-480, Boston Bio Products), 100 mM PMSF (Cat. #: BP-481, Boston Bio Products), and 500 mM EDTA. Following the addition of RIPA cocktail to each sample (100 mg/ml), the lysates were incubated on ice for 15 min before being sonicated for 0.5-1 min to achieve complete homogenization using Sonic Dismembrator (Fisher Scientific Springfield Township, NJ USA). The samples were then centrifuged at 13000 rpm in a Sorvall Legend Micro 21R Centrifuge for 30 min to collect the supernatant fraction of each sample. Total protein concentrations were determined by using an iMark™ Microplate Absorbance Reader (Bio-Rad, Hercules CA). Twenty micrograms of each sample were mixed with an equal volume of 2× sample buffer and electrophoresed on 10% SDS polyacrylamide gels. After the separated proteins were transferred to PVDF membranes (Bio-Rad), the membranes were blocked in 5% skim milk buffer for 2 h, then were incubated at 4° C. with the appropriate primary antibodies overnight. The primary antibodies used included: rabbit polyclonal heat shock protein 70 (HSP70)/HSC-70 (H-300) antibody (1:1000; SC-33575, Santa Cruz Biotechnology); mouse monoclonal NKCC1 (A-6) antibody (1:1000; SC-514774. Santa Cruz Biotechnology); and rabbit polyclonal Anti-Phospho NKCC1 Thr212/Thr217 antibody (1:1000; ABS 1004, EMD Millipore, Burlington, MA, USA). The membranes were subsequently washed 3× with 1×TTBS and incubated with appropriate secondary antibodies in blocking buffer. The secondary antibodies included: goat anti-rabbit IgG-horseradish peroxidase (HRP) antibody (1:5000; SC-2004, Santa Cruz Biotechnology) and goat anti-mouse IgG-HRP antibody (1:5000; SC-2005, Santa Cruz Biotechnology). After 1 h at room temperature. The membranes were washed 3× with 1×TTBS. Bound antibodies were visualized with Luminol/Oxidizing solution, an HRP-based Chemiluminescent Substrate (Boston Bio Product) and quantified with Image J software (ImageJ, U. S. National Institutes of Health. Bethesda, Maryland, USA). The blots were subsequently incubated with 1× stripping buffer, 1× phosphate-buffered saline (PBS), and 1×TTBS for 30 min, then were incubated in blocking buffer for 1 h. After an additional incubation with mouse monoclonal IgG (i-actin (C4) HRP antibody (1:2500; SC-47778, Santa Cruz Biotechnology) in blocking buffer for 1 h, the blots were washed 3× with 1×TTBS and then were imaged with Luminal/Oxidizing solution (Boston Bio Product). Bands were quantified with Image J software.

Example 6: Anodal Multi-Site DCS Reduces Expression of SOD1 Protein

Aggregation of SOD1 is a pathological feature of a subset of familial ALS (Paré et al., "Misfolded SOD1 pathology in sporadic amyotrophic lateral sclerosis", Sci. Rep., 2018). Cliquez ou appuyex ici pour entrer do texte., and the transgenic SOD1-G93A mouse model overexpresses mutant SOD1 (mSOD1) protein, leading to a pathological aggregation. FIGS. 8A-8F show reduced SOD1 expression in SOD1-G93A mice treated with anodal multi-site DCS. FIGS. 8A-8E are photomicrographs of spinal cords of treated and untreated animals. FIG. 8F shows significantly lower mSDO1 expression in stimulated carrier animals as compared to non-stimulated carriers. N=control: 8 slices from 4 animals; stimulated: 5 slices from 5 animals.

Example 7: Anodal Multi-Site DCS Induces an HSP70 Response

Figure 9:
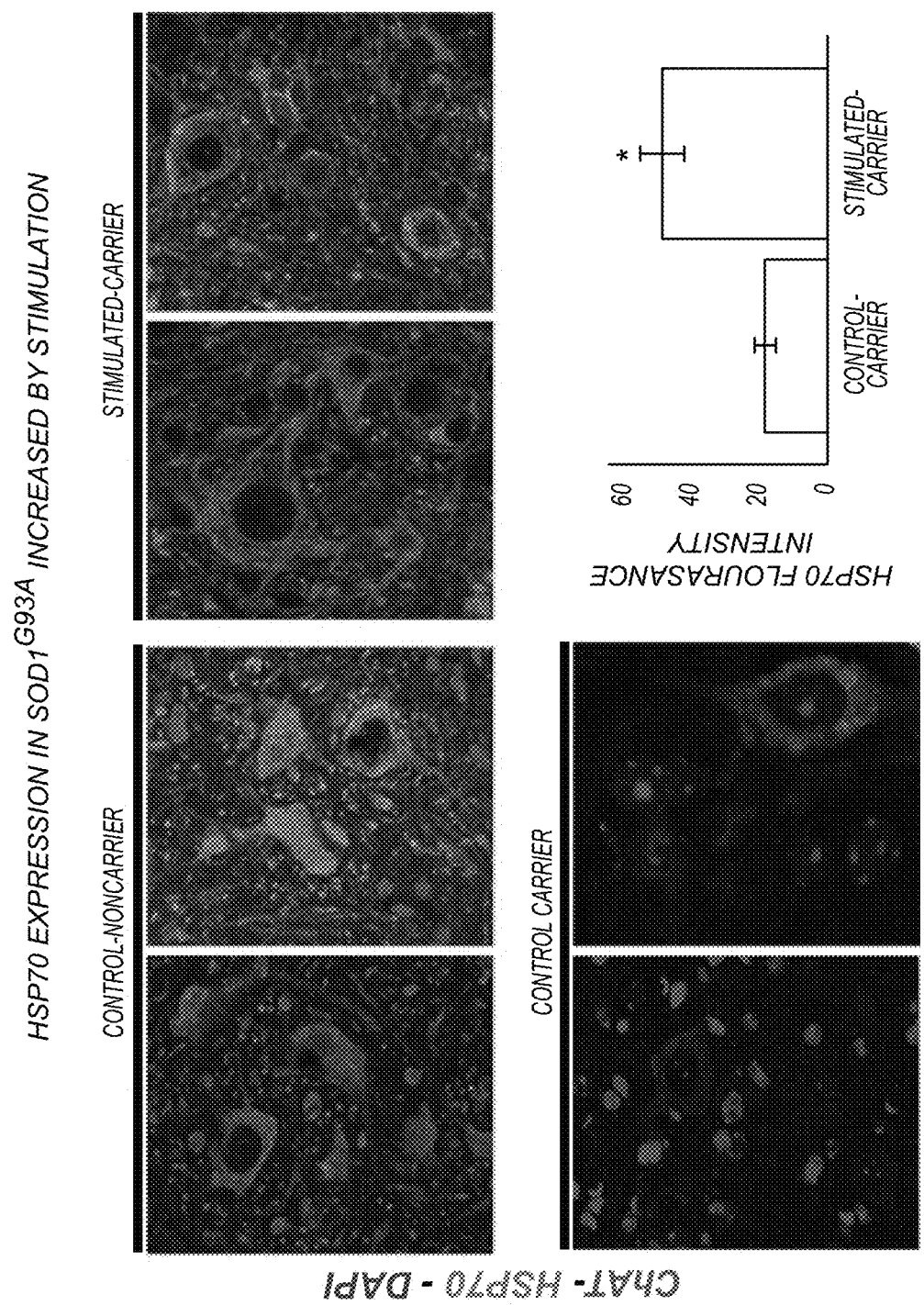
FIG. 9 shows HSP70 expression is reduced in carrier animals as versus non-carrier animals, and is increased in carrier animals after stimulation with anodal multi-site DCS in SOD1-G93A mice. HSP70 is a chaperone protein known to enhance flow of substrates through degradation pathways. HSP70 immunofluorescence intensity of single spinal motor neurons was calculated using ImagJ. HSP70 levels in the spinal cord are significantly reduced in carrier non-stimulated mice (bottom left) as compared to control mice (top left), but it is significantly increased in carrier mice after stimulation (top right). These findings are summarized in a bar graph (bottom right; N=stimulated: 27 motor neurons from 4 animals; control: 19 motor neurons from 3 animals).

HSP70 is a chaperone protein known to enhance flow of substrates through degradation pathways. FIG. 9 shows HSP70 expression is reduced in carrier animals as versus non-carrier animals, and is increased in carrier animals after stimulation with anodal multi-site DCS in SOD1-G93A mice. HSP70 immunofluorescence intensity of single spinal motor neurons was calculated using ImagJ. HSP70 levels in the spinal cord are significantly reduced in carrier non-stimulated mice (bottom left) as compared to control mice (top left), but it is significantly increased in carrier mice after stimulation (top right). These findings are summarized in a bar graph (bottom right; N=stimulated: 27 motor neurons from 4 animals; control: 19 motor neurons from 3 animals).

Immunohistochemistry

HSP70 Immunohistochemistry: To examine HSP70 expression in motor neurons following stimulation with multi-site DCS, animals were anesthetized with a ketamine/xylazine solution and then perfused with PBS at room temperature, followed by 4% paraformaldehyde. Dissected spinal cord segments were post-fixed overnight in the same fixative and then were transferred to 30% sucrose for cryoprotection. The spinal cord segments were frozen with dry ice, sectioned, and collected in Phosphate Buffer Saline (PBS). After three washes in Tris A buffer, the sections were washed 1× with Tris B for 15 min and then were blocked in 10% Normal Goat Serum (NGS) diluted in Tris B. After 1 h, primary mouse monoclonal HSP70 (F-3) antibody was added (1:500, sc-373867, Santa Cruz Biotechnology) and the sections were incubated overnight on a shaker at 4 C. The next day, the sections were washed 3× and then were incubated with a biotinylated goat anti-mouse antibody (1:500: BA-9200, Vector Laboratories Burlingame, CA USA). After 1 h, DyLight 488 (1:2000: SA-5488, Vector Laboratories) was added. After another 30 min, the sections were washed 2× with Tris A before the slices were mounted with medium containing DAPI (H-1200: Vector Laboratories).

Choline acetyltransferase (ChAT) Immunohistochemistry: Spinal cord sections were washed 3× with PBS before being incubated with 10% rabbit serum/0.1'Y° Triton X-100/0.1 M PBS for 1 h at room temperature. The sections were then incubated with an anti-ChAT primary antibody (1:500, AB144P, EMD Millipore Corp.) in 0.1% Triton X-100/0.1 M PBS for 48-72 h at 4 C. The sections were thoroughly washed 3× with PBS and then were incubated with rabbit anti-goat 568 nm antibodies (1:500) in 0.1% Triton X-100/0.1 M PBS for 1 h at room temperature. After an additional three washes with PBS, the sections were mounted with medium containing DAPI (H-1200; Vector Laboratories).

q-PCR

RNA was isolated from spinal cord samples by using a Trizol-based method (Rio et al., 2010), followed by extraction with chloroform and isopropyl alcohol. Briefly, each RNA sample was dissolved in diethyl dicarbonate (DEPC) water and then purified with a Qiagen RNAeasy kit (Qiagen, Hilden Germany), according to the manufacturer's instructions. RNA concentrations were measured with a Nanodrop 2000c instrument (Thermofisher Scientific, Waltham, MA, USA). Total RNA was converted to complementary DNA (cDNA) with the iScriptT" Reverse Transcription Supermix (Bio-Rad, Hercules, CA, USA). For each reaction, 2 pg of total RNA was combined with gene specific primers (PrimePCR Assay Slc12a2). Samples that were obtained from stimulated and unstimulated animals were always assayed on the same plate. For each sample, amplified product differences for each transcript were measured from three replicates by using SYBR Green chemistry-based detection. Beta-actin (ACTB), TATA box binding protein (TBP), and hypoxanthine phosphoribosyltransferase 1 (HPRT1) were used as endogenous reference genes, and the primers used for amplification of these genes were PrimePCR Assay ACTB, PrimePCR Assay TBP, and PrimePCR Assay HPRT1, respectively. The resulting three transcripts were selected for analysis based on a previous demonstration of their stable expression in the central nervous system (Valente et al., 2014; Walder et al., 2014). The total reaction volume was 10 µl and it included: 5 µl of the supermix, primers, cDNA template, and nuclease-free water. The qPCR reactions were carried out in 384-well plates with the CFX384 Real Time System (Bio-Rad) and SsoAD-VANCED Universal SYBR Green Supermix (Bio-Rad). CFX manager software (Hercules, California USA) was used with automatic baseline and threshold detection options selected. The resulting data were exported to Microsoft Excel and relative normalized expression was calculated for each sample by using the geometric mean of the triplicates against the endogenous reference genes as a normalization factor.

Example 8: Anodal Multi-Site DCS Reduces Expression of Phosphorylated Tau

Figure 10:
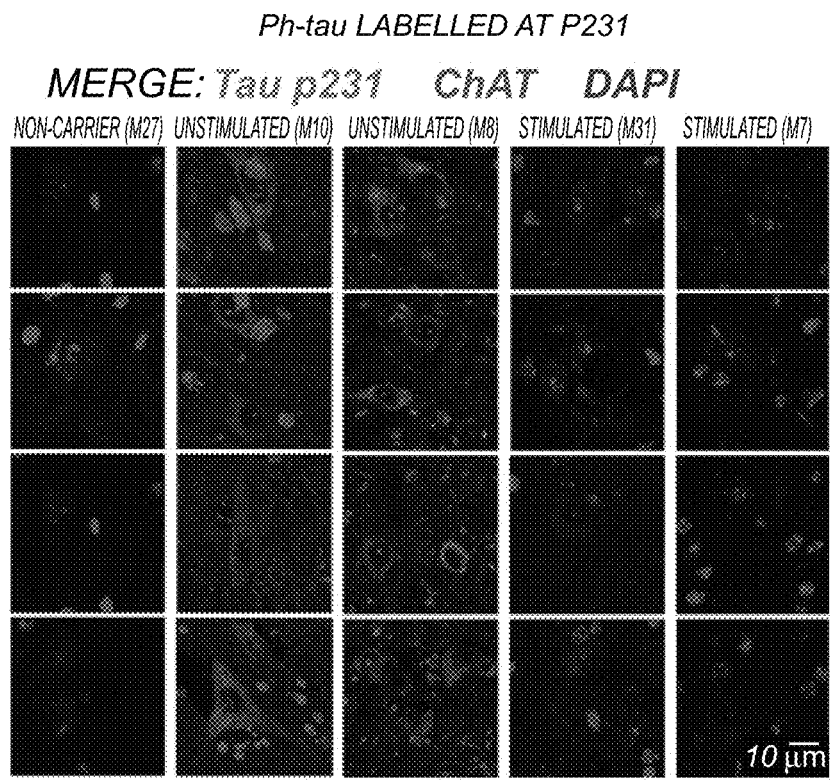
FIG. 10 shows the effects of anodal multi-site DCS on levels of phosphorylated tau protein (phTau). Increased phosphorylated tau has been reported in ALS (Stevens et al., "Increased tau phosphorylation in motor neurons from clinically pure sporadic amyotrophic lateral sclerosis patients", J. Neuropathol. Exp. Neurol., 2019). More phTau is found in non-stimulated carrier mice as compared with non-carriers. Treatment with anodal multi-site DCS reduced phTau levels in carrier mice.

Increased phosphorylated tau protein (phTau) has been reported in ALS (Stevens et al., "Increased tau phosphorylation in motor neurons from clinically pure sporadic amyotrophic lateral sclerosis patients", *J. Neuropathol. Exp. Neurol.*, 2019). FIG. 10 shows the effects of anodal multi-site DCS on levels of phosphorylated tau protein (phTau). There is a higher level of phTau found in non-stimulated carrier mice as compared with non-carriers. Treatment with anodal multi-site DCS reduced phTau levels in carrier mice.

Example 9: Anodal Multi-Site DCS Induces Increased Expression of LC3B

We investigated the expression of LC3B (microtubule-associated protein-1 light chain 3 beta) in SOD1-G93A mice. LC3B is a protein marker for autophagy activity. Autophagy dysregulation has been associated with ALS and decreased LC3B could lead to accelerated motor neuron degradation following abnormal accumulation of toxic proteins. FIG. 11 shows the effects of anodal multi-site DCS on the expression of LC3B in SOD1-G93A mice. LC3B is a protein marker for autophagy activity. LC3B expression is increased in carrier mice after stimulation as compared to non-stimulated carrier mice (control).

Example 10: Anodal Multi-Site DCS Increases Survival of Spinal Motor Neurons

Figure 12:
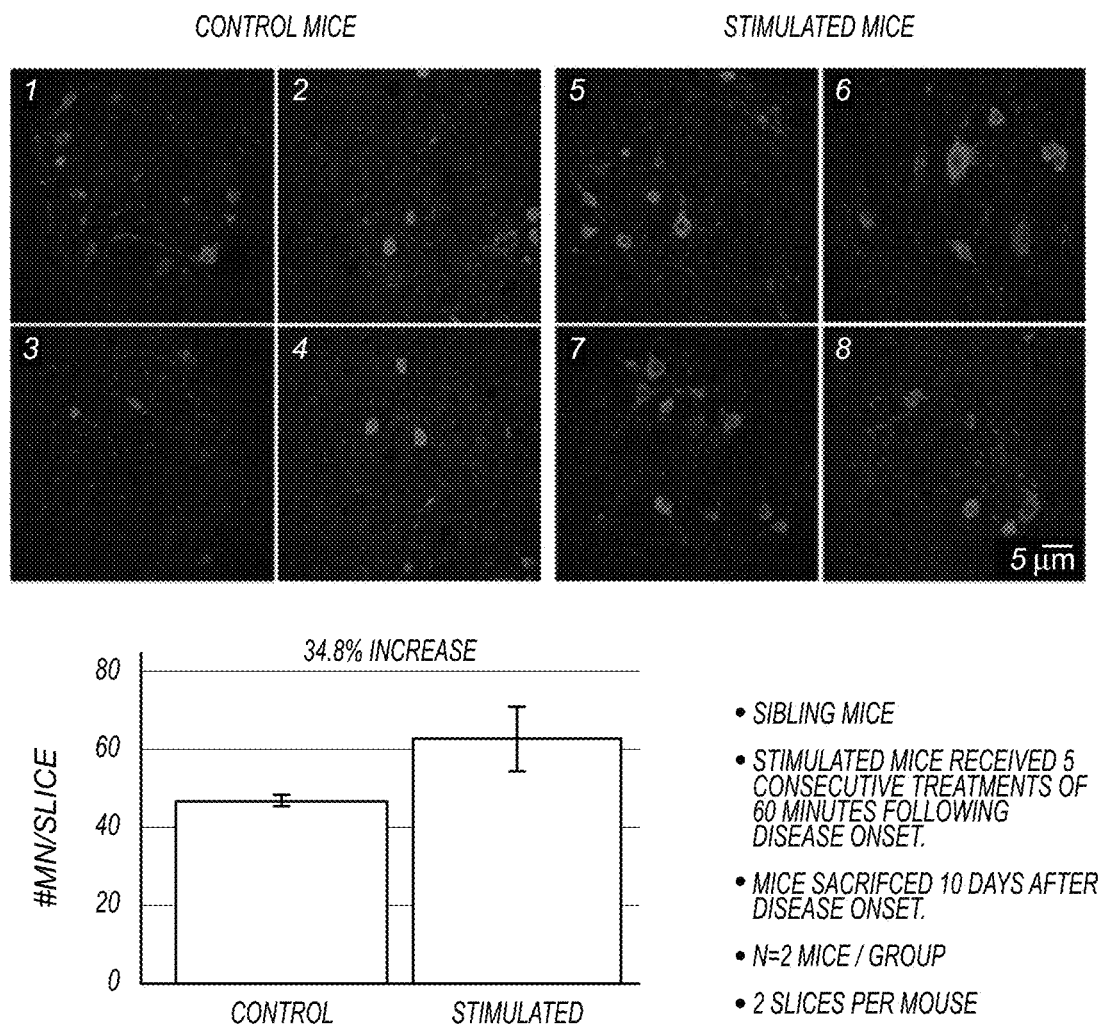
FIG. 12 exhibits the effects of anodal multi-site DCS on the survival of spinal motor neurons of SOD1-G93A mice. Sibling SD1-G93A mice were separated into stimulated and non-stimulated groups. Stimulated mice received 5 consecutive daily treatments of 60 minutes following disease onset. Mice were sacrificed 10 days after disease onset. Motor neurons were counted after 2 slices were extracted per mouse. Micrographs show 4 sections of the same slice for each example mouse. Stimulation resulted in the preservation of larger alpha motor neurons and an overall 34.8% increase in motor neuron count after stimulation as compared to non-stimulated carriers.

In ALS, motor neuron hyperexcitability results in eventual motor neuron death. We examined the effect of multi-site DCS on motor neuron survival. FIG. 12 exhibits the effects of anodal multi-site DCS on the survival of spinal motor neurons of SOD1-G93A mice. Sibling SD1-G93A mice were separated into stimulated and non-stimulated groups. Stimulated mice received 5 consecutive daily treatments of 60 minutes following disease onset. Mice were sacrificed 10 days after disease onset. Motor neurons were counted after 2 slices were extracted per mouse. Micrographs show 4 sections of the same slice for each example mouse. Stimulation resulted in the preservation of larger alpha motor neurons and an overall 34.8% increase in motor neuron count after stimulation as compared to non-stimulated carriers.

Example 11: Anodal Multi-Site DCS Increases Survival of SOD1-G93A Mice

Figure 13:
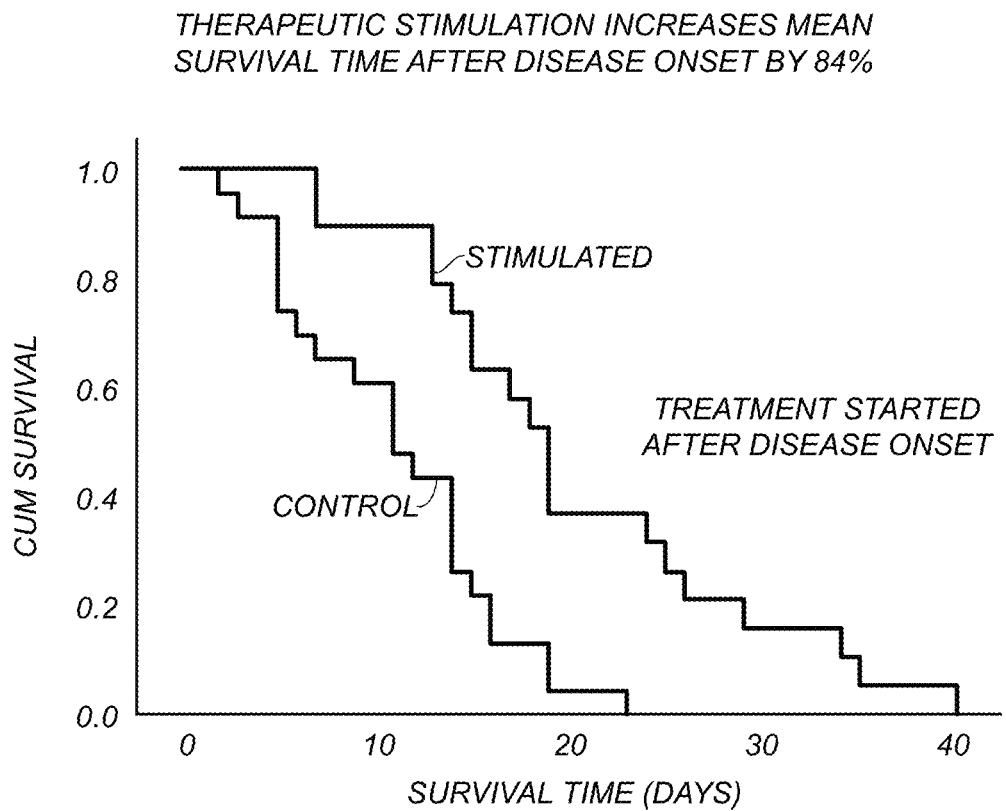
FIG. 13 is a Kaplan-Meier plot showing the effects of anodal multi-site DCS on the survival of SOD1-G93A mice when treatment starts immediately after symptom onset (therapeutic stimulation paradigm). Symptom onset was defined as a score of 80 or less in the grid walking test. Stimulated carrier mice survived for 20.5 days (±2.1 days) on average while non-stimulated carrier mice survived for 11.1 days (±1.2 days) on average, leading to an 84% increase in mean survival time after disease onset for stimulated mice. N=19 stimulated mice; 23 non-stimulated mice. Log Rank (Mantel-Cox), Chi-Square=13.86, p=0.0002; Breslow (Generalized Wilcoxon) Chi-Square=12.25, p=0.0005; Tarone-Ware, Chi-Square=13.12, p=0.0003.

Our premise is that since multi-site DCS can suppress hyperexcitable spinal motor neurons and, it might have effects beyond motor function. Using a therapeutic stimulation paradigm (5 days/week, 3.3 A/m² current density) in SOD1-G93A mice (starting at disease onset), we assessed survival in control vs. stimulated mice (gender balanced between groups). FIG. 13 is a Kaplan-Meier plot showing the effects of anodal multi-site DCS on the survival of SOD1-G93A mice when treatment starts immediately after symptom onset. Symptom onset was defined as a score of 80 or less in the grid walking test. Stimulated carrier mice survived for 20.5 days (±2.1 days) on average while non-stimulated carrier mice survived for 11.1 days (±1.2 days) on average, leading to an 84% increase in mean survival time after disease onset for stimulated mice. N=19 stimulated mice; 23 non-stimulated mice. Log Rank (Mantel-Cox), Chi-Square=13.86, p=0.0002; Breslow (Generalized Wilcoxon) Chi-Square=12.25, p=0.0005; Tarone-Ware, Chi-Square=13.12, p=0.0003.

Figure 14:
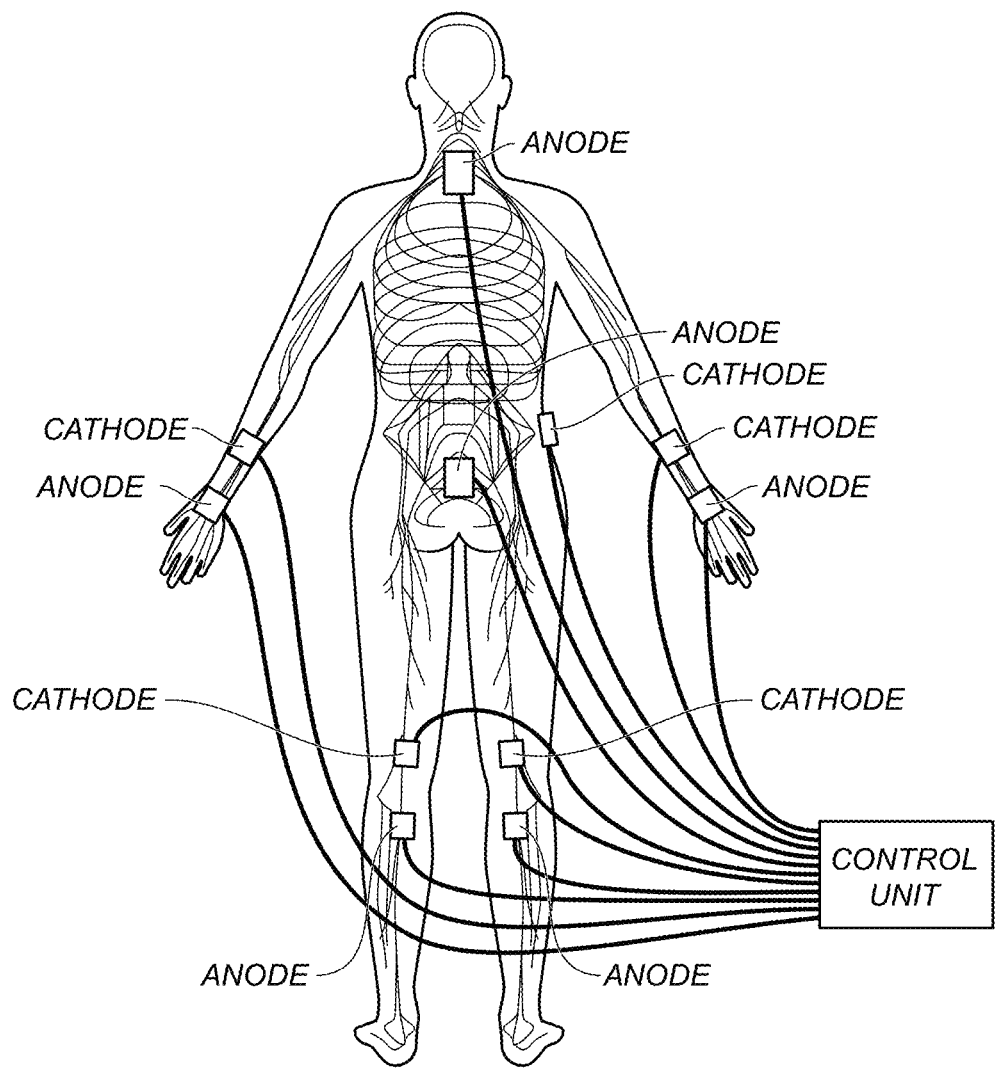
FIG. 14 illustrates an embodiment of a novel hyperexcitability suppression approach to treating ALS consisting of a control unit applying multi-site DCS and skin-surface electrodes applied along the spinal column and the peripheral nerves of the four limbs.
Figure 16:
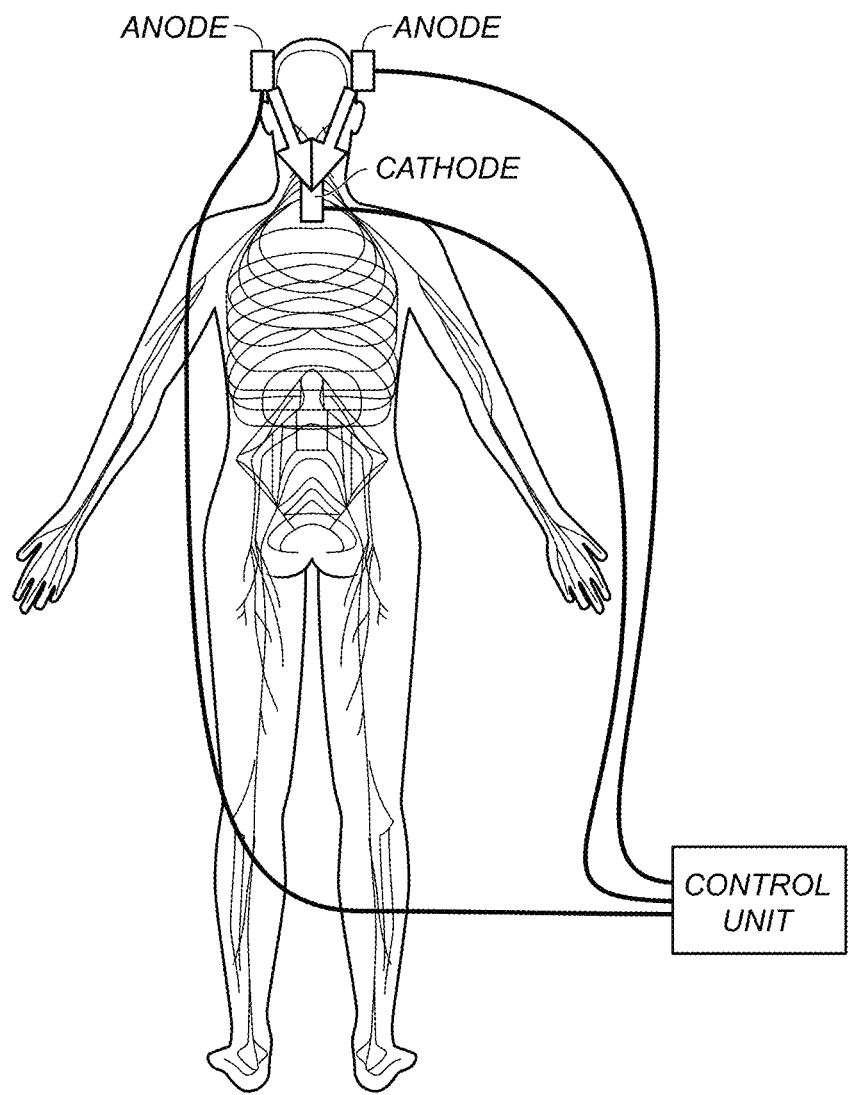
FIG. 16 illustrates an embodiment of a multi-channel cortical stimulation device utilized to preserve cortical neurons using the same multi-site DCS technology.

Example 12: Embodiment of Hyperexcitability Suppression Approach in Humans with ALS FIG. 14 illustrates an embodiment of a novel hyperexcitability suppression approach to treating ALS consisting of a control unit applying multi-site DCS and skin-surface electrodes applied along the spinal column and the peripheral nerves of the four limbs. Anodes are positioned along the spinal column with a return electrode on the anterior iliac crest. Peripheral electrodes are positioned on each limb, with cathode positioned more proximally than anode. Current from the spinal anode flows both across the spinal cord (to return electrode) and down the limb (to peripheral cathodes). FIG. 15 shows an embodiment of a multi-channel unit that is used to sequentially treat ALS patients from the cervical to the lumbar spine to reduce spasticity and slow down disease progression. Each channel is limited to sourcing no more than 5 mA DC with a maximum current density of 0.56 mA/cm² for the smallest electrodes (below safety limits specified by applicable standards). FIG. 16 illustrates an embodiment of using bi-hemispheric cortical stimulation to preserve cortical neurons using the same multi-site DCS technology. Current flows from the cortical anodes to the spinal cathode.

In summary, the present results demonstrate that anodal multi-site DCS (a) reduces neuronal spinal excitability long-term, (b) slows the progression of muscle weakness, and (c) significantly increases lifespan of stimulated SOD1-G93A mice by 84%. Additionally, we found that treatment with anodal multi-site DCS: (a) reduces the expression of mutant SOD1 protein, (b) reduces expression of elevated NKCC1, (c) reduces expression of elevated tau, (d) increases expression of HSP70, and (e) increases expression of LC3B. Together, these data provide evidence that anodal multi-site DCS enhances clearance of misfolded proteins by modulating the proteolytic systems of autophagy and the proteasome. By reducing spinal excitability and clearing toxic proteins from spinal cells, multi-site DCS could become a disease-modifying therapeutic intervention against ALS.

What is claimed is:

1. A stimulation device for treating motor neuron disease by regulating biological activity associated with one of the spinal cord, the brain or a peripheral nerve, comprising:
a direct current voltage source having a plurality of terminals
a first of the terminals for connecting a first electrode of a first pair of electrodes to the direct current voltage source; the first electrode being at or proximate to a dorsal aspect of a spinal cord of a vertebrate being, on a cranium of a vertebrate being or at or proximal to a peripheral nerve of a vertebrate being;
a second of the terminals for connecting a second electrode of said first pair of electrodes to the direct current voltage source; the second electrode being placed at a position remote from the first electrode; the first and second electrodes being oppositely charged and configured to form a direct current path for stimulating at least one of said spinal cord, said cranium and said peripheral nerve;
a controller component configured to provide direct current flow in said direct current path, for stimulation of at least one of said spinal cord, said cranium and said peripheral nerve;
said controller component configured to provide said direct current flow at an intensity, polarity and for a period of time across any one of said spinal cord, said cranium and said peripheral nerve for stimulation to effect: i) a decrease in biological activity of, or level of gene expression, or protein expression, of any member of the set of the following biological macromolecules: NKCC1, SOD1, and tau, and ii) an increase in biological activity of, or level of gene expression or protein expression, of any member of the set of the following biological macromolecules: HSP70 and LC3B, for treatment of motor neuron disease at at least one of said spinal cord, brain, and peripheral nerve.

2. The stimulation device of claim 1, wherein said controller component is further configured to provide said direct current flow at an intensity and polarity to change biological activity of or level of gene expression and/or protein expression, for stimulation of ALS-associated genes, including any of FUS (FUS protein), TARDBP (TDP-43 protein), and C9orf72 (C9orf72 protein), at at least one of said spinal cord, brain, and peripheral nerve.

3. The stimulation device of claim 1, further including a plurality of said electrodes for forming a plurality of pairs of said electrodes; a second pair of said terminals for forming a second pair of electrodes, said second pair of electrodes connecting to said direct current voltage source; the first pair of electrodes for stimulation of a first location on said being and said second pair of electrodes for stimulation of a second location on said being, said locations selected as at or proximate to said dorsal aspect of said spinal cord, and on said cranium, and at said peripheral nerve, to deliver multi-site stimulations simultaneously at one or more of said macromolecules simultaneously at least one of said spinal cord, brain, and peripheral nerve.

4. The stimulation device of claim 1, wherein said motor neuron disease is a disease selected from the group consisting of amyotrophic lateral sclerosis, primary lateral sclerosis, progressive muscular atrophy, progressive bulbar palsy, spinal muscular atrophy and post-polio syndrome.

5. The stimulation device of claim 1, wherein the controller component is configured to provide said current flow including at least one of constant, continuous, pulsed, intermittent, varying, and non-varying current flow.

6. The stimulation device of claim 1, wherein at least one of the first and second electrodes is implanted.

7. The stimulation device of claim 1, wherein at least one of the controller component and the direct current voltage source are disposed in a wearable housing.

8. The stimulation device of claim 3, wherein said biological activity of or said level of gene expression and/or protein expression of any of NKCC1, SOD1 and tau is decreased.

9. The stimulation device of claim 3, wherein said biological activity of or said level of gene expression and/or protein expression of any of HSP70 and LC3B is increased.

10. A method of treating motor neuron disease selected from the group including amyotrophic lateral sclerosis, primary lateral sclerosis, progressive muscular atrophy, progressive bulbar palsy, spinal muscular atrophy and post-polio syndrome, in a vertebrate being, comprising the steps of:
   Defining an anodal direct current flow path between an A electrode and a B electrode pair of a direct current source, wherein the direct current is at least one of constant, continuous, pulsed, intermittent, varying and non-varying,
   Applying the direct current flow for stimulation between said A electrode and B electrode pair with the A and B electrodes oppositely charged, and the A electrode as anode and being at a position at or proximate to a first location of a dorsal aspect of a spinal cord of a vertebrate being or with the A electrode being at a first location on a cranium of a vertebrate being; and
   Placing the B electrode as cathode at a second position remote from the A electrode position, and
   Applying said anodal direct current flow at an intensity and for a period of time to modulate biological activity of or level of gene expression and/or protein expression levels of a target protein associated with treatment of a motor neuron disease, and
   Providing said anodal direct current flow to effect at least one of i) a decrease in the biological activity of, or level of gene expression of, or level of protein expression of, at least one of the following biological macromolecules: NKCC1, SOD1, and tau, and ii) an increase in biological activity of, or level of gene expression or level of protein expression of, at least one of the following biological macromolecules: HSP70 and LC3B, in said being.

11. The method of claim 10, further comprising the steps of:
   moving said A electrode to a second location of a dorsal aspect of a spinal cord of a vertebrate being or to a second location on a cranium of a vertebrate being;
   placing said B electrode at a second position remote from the A electrode; and
   applying the direct current stimulation at an intensity and for a period of time sufficient to modulate biological activity of or level of gene expression and/or protein expression levels of a target protein associated with ALS.

12. The method of claim 11, further comprising repeating the treatment one or more times.

13. The method of claim 10, wherein a plurality of A electrodes are located at or proximate to a plurality of positions along the dorsal aspect of the spinal cord and a plurality of B electrodes are placed at positions remote from the plurality of A electrodes.

14. The method of claim 13, wherein a plurality of A electrodes are located at a plurality of positions on the cranium associated with movement control and a plurality of B electrodes are placed at positions remote from the plurality of A electrodes.

15. The method of claim 14, wherein said stimulation applied between the plurality of A and B electrodes is applied simultaneously or sequentially.

16. A method of treating ALS in a vertebrate being, comprising the steps of:
   applying a first stimulation between an A electrode and a B electrode of a direct current source with the A electrode being at or proximate to a first location of a dorsal aspect of a spinal cord of a vertebrate being;
   applying a second stimulation between a C electrode and a D electrode of a direct current source with the C electrode being at a first location on a cranium of a vertebrate being; and
   applying the direct current stimulation at an intensity and for a period of time sufficient to modulate biological activity of or level of gene expression and/or protein expression levels of a target protein associated with ALS;
   placing the B electrode at a position remote from the A electrode and the A and B electrodes are oppositely charged, and the D electrode is placed at a position remote from the C electrode and the C and D electrodes are oppositely charged,
   wherein the direct current is at least one of constant, continuous, pulsed, intermittent, varying and non-varying;
   provide said direct current flow at an intensity, polarity and for a period of time to effect at least one of i) a decrease in biological activity of, or level of gene expression, or protein expression, of at least one of the following biological macromolecules: NKCC1, SOD1, and tau, and ii) an increase in biological activity of, or level of gene expression or protein expression of, at least one of the following biological macromolecules: HSP70 and LC3B, in said being.

17. The method of claim 16, wherein the first and second stimulations are applied simultaneously or sequentially.

18. The method of claim 16, further comprising the steps of:
   moving said A electrode to a second location of a dorsal aspect of a spinal cord of a vertebrate being;
   placing said B electrode at a second position remote from the A electrode; and
   applying the direct current stimulation at an intensity and for a period of time sufficient to modulate biological activity of or level of gene expression and/or protein expression levels of a target protein associated with ALS.

19. The method of claim 16, further comprising the steps of:
   moving said C electrode to a second location on a cranium of a vertebrate being;
   placing said D electrode at a second position remote from the C electrode; and
   applying the direct current stimulation at an intensity and for a period of time sufficient to modulate biological activity of or level of gene expression and/or protein expression levels of a target protein associated with ALS.

20. The method of claim 19, further comprising repeating the steps one or more times.

21. The method of claim 19, wherein a plurality of A electrodes are located at or proximate to a plurality of positions along the dorsal aspect of the spinal cord and a plurality of B electrodes are placed at positions remote from the plurality of A electrodes.

22. The method of claim 19, wherein a plurality of C electrodes are located at a plurality of positions on the cranium associated with movement control and a plurality of D electrodes are placed at positions remote from the plurality of C electrodes.

23. The method of claim 21, wherein said stimulation applied between the plurality of A and B electrodes and between the plurality of C and D electrodes is applied simultaneously or sequentially.

24. The method of claim 16, further comprising the step of:
applying a third stimulation between an E electrode and an F electrode of a direct current source with the E electrode being at or proximate to a first location of a first peripheral nerve of a vertebrate being; and
wherein the F electrode is placed at a position remote from the E electrode and the E and F electrodes are oppositely charged.

25. The method of claim 24, wherein the first, second and third stimulations are applied simultaneously or sequentially.

26. The method of claim 24, further comprising the steps of:
moving said E electrode to a second location at or proximate to the first peripheral nerve or to a location at or proximate to a second peripheral nerve;
optionally placing said F electrode at a second position remote from the E electrode; and
applying the direct current stimulation at an intensity and for a period of time sufficient to modulate biological activity of or level of gene expression and/or protein expression levels of a target protein associated with ALS.

27. The method of claim 26, further comprising repeating the steps one or more times.

28. The method of claim 24, wherein a plurality of E electrodes are located at a plurality of positions along the peripheral nerve or are located at or proximate to a plurality of peripheral nerves and a plurality of F electrodes are placed at positions remote from the plurality of E electrodes.

29. The method of claim 28, wherein said stimulation applied between the plurality of E and F electrodes is applied simultaneously or sequentially.

30. The method of claim 24, wherein said peripheral nerve innervates a skeletal muscle.

31. The method of claim 24, wherein said period of time comprises a series of stimulation sessions on 1 or more days, the days being consecutive or non-consecutive.

32. The method of claim 16, wherein said biological activity of or said level of gene expression and/or protein expression of NKCC1, SOD1 or tau is decreased.

33. The method of claim 16, wherein said biological activity of or said level of gene expression and/or protein expression of HSP70 or LC3B is increased.

* * * * *